(12) United States Patent
Evans et al.

(10) Patent No.: US 12,403,016 B2
(45) Date of Patent: Sep. 2, 2025

(54) BONE GRAFT AND METHOD OF MAKING AND USING SAME

(71) Applicant: LifeNet Health, Virginia Beach, VA (US)

(72) Inventors: Mark Evans, Virginia Beach, VA (US); Dennis Phelps, Virginia Beach, VA (US); Jingsong Chen, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

(21) Appl. No.: 18/528,148

(22) Filed: Dec. 4, 2023

(65) Prior Publication Data

US 2024/0099856 A1    Mar. 28, 2024

Related U.S. Application Data

(63) Continuation of application No. 17/870,380, filed on Jul. 21, 2022, now Pat. No. 11,865,015, which is a
(Continued)

(51) Int. Cl.
*A61F 2/44* (2006.01)
*A61F 2/28* (2006.01)
*A61F 2/30* (2006.01)

(52) U.S. Cl.
CPC .......... *A61F 2/4465* (2013.01); *A61F 2/2846* (2013.01); *A61F 2/447* (2013.01);
(Continued)

(58) Field of Classification Search
CPC .......... A61F 2/44; A61F 2/4455; A61F 2/446; A61F 2/4465; A61F 2/447;
(Continued)

(56) References Cited

U.S. PATENT DOCUMENTS 5,820,581 A * 10/1998 Wolfinbarger, Jr. ........................ A61F 2/4644
128/898
6,719,794 B2 * 4/2004 Gerber .................. A61F 2/4465
623/17.11

(Continued)

FOREIGN PATENT DOCUMENTS

| WO | 03047473 A2 | 6/2003 |
| WO | 2006096514 A2 | 9/2006 |
| WO | 2014145527 A2 | 9/2014 |

OTHER PUBLICATIONS

Extended European Search Report for European Application No. 17 753 787.5, dated Sep. 16, 2019, 11 pages.
(Continued)

*Primary Examiner* — Eric S Gibson
(74) *Attorney, Agent, or Firm* — Matney Legal Group PLLC

(57) ABSTRACT

A spinal bone graft includes one or more cortical bone portions forming a first unit. The first unit includes an engagement surface for contacting bone, and a mating surface. The mating surface forms at least one first undercut. The bone graft also includes one or more cortical bone portions forming a second unit. The second unit includes an engagement surface for contacting bone, and a mating surface. The mating surface forms either at least one second undercut, or at least one connector. In the former, at least one connector is received in each of the first and second undercuts to interconnect the first and second units. In the latter, the at least one connector of the second unit is received in the first undercut of the first unit to interconnect the first unit and second unit.

14 Claims, 12 Drawing Sheets

Related U.S. Application Data continuation of application No. 17/092,781, filed on Nov. 9, 2020, now Pat. No. 11,395,746, which is a continuation of application No. 15/999,105, filed as application No. PCT/US2017/018057 on Feb. 16, 2017, now Pat. No. 10,857,000.

(60) Provisional application No. 62/296,925, filed on Feb. 18, 2016.

(52) U.S. Cl.
CPC ............. *A61F 2002/2839* (2013.01); *A61F 2002/30057* (2013.01); *A61F 2002/30125* (2013.01); *A61F 2002/30153* (2013.01); *A61F 2002/30158* (2013.01); *A61F 2002/3036* (2013.01); *A61F 2002/30677* (2013.01)

(58) Field of Classification Search
CPC .... A61F 2002/2893; A61F 2002/30004; A61F 2002/30057; A61F 2002/30059; A61F 2002/30062; A61F 2002/30125; A61F 2002/30138; A61F 2002/30143; A61F 2002/30146; A61F 2002/30149; A61F 2002/30153; A61F 2002/30156; A61F 2002/30158; A61F 2002/30166; A61F 2002/30224; A61F 2002/3023; A61F 2002/30266; A61F 2002/30281; A61F 2002/30331; A61F 2002/30354; A61F 2002/30355; A61F 2002/3036; A61F 2002/30387; A61F 2002/30677; A61F 2002/30904; A61F 2002/3093
See application file for complete search history.

(56) References Cited

U.S. PATENT DOCUMENTS

| | | | | |
|---|---|---|---|---|
| 8,182,532 | B2* | 5/2012 | Anderson | A61L 27/36 623/17.11 |
| 9,585,764 | B2* | 3/2017 | McKay | A61F 2/4455 |
| 9,770,340 | B2* | 9/2017 | Zaveloff | A61F 2/442 |
| 10,857,000 | B2* | 12/2020 | Evans | A61F 2/4455 |
| 11,395,746 | B2* | 7/2022 | Evans | A61F 2/4455 |
| 11,865,015 | B2* | 1/2024 | Evans | A61F 2/4465 |
| 2004/0078078 | A1* | 4/2004 | Shepard | A61F 2/447 623/17.11 |
| 2006/0241763 | A1* | 10/2006 | Paul | A61F 2/4644 623/17.11 |
| 2007/0270957 | A1* | 11/2007 | Heinz | A61F 2/4465 623/17.11 |
| 2008/0154379 | A1* | 6/2008 | Steiner | A61F 2/4455 623/17.16 |
| 2009/0099661 | A1* | 4/2009 | Bhattacharya | A61F 2/4455 623/17.11 |
| 2010/0168798 | A1* | 7/2010 | Clineff | A61C 8/0012 606/279 |
| 2013/0204374 | A1* | 8/2013 | Milella, Jr. | A61F 2/4611 623/17.16 |
| 2013/0231747 | A1* | 9/2013 | Olmos | A61F 2/4611 623/17.16 |
| 2013/0282128 | A1* | 10/2013 | McKay | A61F 2/4465 623/18.11 |
| 2014/0121777 | A1* | 5/2014 | Rosen | A61F 2/4455 623/17.16 |
| 2015/0045892 | A1* | 2/2015 | Lynn | A61B 17/1671 623/17.16 |
| 2015/0173902 | A1* | 6/2015 | Southard | A61F 2/44 623/23.51 |
| 2020/0060843 | A1* | 2/2020 | Evans | A61F 2/4455 |
| 2021/0052396 | A1* | 2/2021 | Evans | A61F 2/2846 |
| 2022/0354666 | A1* | 11/2022 | Evans | A61F 2/447 |
| 2024/0099856 | A1* | 3/2024 | Evans | A61F 2/2846 |

OTHER PUBLICATIONS

International Search Report and Written Opinion for International Application No. PCT/US2017/018057, dated Jun. 30, 2017, 18 pages.

Entire patent prosecution history of U.S. Appl. No. 15/999,105, filed Aug. 17, 2018, entitled "Bone Graft and Method of Making and Using Same."

Entire patent prosecution history of U.S. Appl. No. 17/092,781, filed Nov. 9, 2020, entitled "Bone Graft and Method of Making and Using Same."

Entire patent prosecution history of U.S. Appl. No. 17/870,380, filed Jul. 21, 2022, entitled "Bone Graft and Method of Making and Using Same."

* cited by examiner

BONE GRAFT AND METHOD OF MAKING AND USING SAME

RELATED APPLICATIONS

This application is a continuation of U.S. patent application Ser. No. 17/870,380, filed Jul. 21, 2022, now allowed, which is a continuation application of U.S. application Ser. No. 17/092,781, filed Nov. 9, 2020, now U.S. Pat. No. 11,395,746, issued on Jul. 26, 2022, which claims priority to U.S. patent application Ser. No. 15/999,105 filed on Aug. 17, 2018, now U.S. Pat. No. 10,857,000, issued on Dec. 8, 2020, which claims priority to PCT/US2017/18057, filed Feb. 16, 2017, which claims the benefit of priority of U.S. Provisional Application No. 62/296,925, filed Feb. 18, 2016, the contents of which are incorporated by reference herein in their entirety.

FIELD

The invention relates generally to bone grafts, and more particularly to bone grafts useful for spinal fusion, as well as methods of making and using the bone grafts.

BACKGROUND

In the field of prosthetic implants, materials often used include bone grafts and implants produced from non-bone materials, including for example stainless steel, titanium and plastics. The choice of whether to use a bone or a non-bone implant often depends on the clinical indication, implant site, whether the implant is load-bearing, and the size of the implant needed.

Prior to the present invention, the use of bone grafts versus non-bone prosthetic implants to, for example, support and fuse together adjacent vertebrae, has been limited in part by the physical size of a cortical bone graft. Interbody bone grafting involves the problem of strength. Strong cortical bone (the outer layer) is required as a strut in the interbody position to prevent collapse of the disc space while healing occurs. Cortical bone obtained from a cadaver source fashioned into struts, is not wide enough for optimum load bearing. As such, a single piece of cortical bone typically cannot be obtained in a volume large enough to make a suitable bone graft for implantation. This natural limitation often discourages the use of a bone graft product.

The success or failure of a bone graft further depends on whether the bone graft remains at the implant site, is cellularized, and whether it can withstand the mechanical load. In spinal surgery, there are two primary indications for use of allograft bone: (1) when there is insufficient available autograft bone, and (2) in spinal fusion procedures when a structural element in needed. Typically, bone grafts are affixed at an implant site by fusion. Bone grafts for spinal applications often fail because they are extruded from the implantation site due to shifting, rotation, and slippage of the graft, are not cellularized, or fail mechanically.

SUMMARY

Bone grafts in accordance with embodiments of the invention can be used in applications that are normally suited only for non-bone prosthetic implants. In particular, bone grafts in accordance with embodiments of the invention utilize an assembly of parts, with each part being small enough so that allograft or autograft material can be used to form each part. Bone grafts described herein also address the problem of graft failure by providing a composite bone graft which can be appropriately sized for any application and made out of strong cortical bone. These bone grafts can promote the ingrowth of patient bone at an implantation site by promoting osteoinductivity and cellularization, provide added stability and mechanical strength, and do not shift, extrude or rotate after implantation.

Composite bone grafts in accordance with embodiments of the invention can feature a number of connector configurations that interconnect components into an assembly. The connector configurations can feature undercut geometries that prevent the connected components from separating in response to tensile forces. In addition, embodiments of the invention can feature connectors that add no additional height, width or depth to the assembly. In particular, grafts in accordance with the invention can feature one or more connectors that connect(s) a first graft unit with a second graft unit, the connectors being received completely within the first graft unit and/or second graft unit so that the net height of the assembled graft is equal to the sum of the individual heights of the first and second graft units. By adding no additional height to the assembled graft, the overall height is minimized. The one or more connectors can be components that are separate from the first and/or second graft units. In addition, or in the alternative, the one or more connectors can be components that are integrally formed with the first graft unit as one unitary body, and/or integrally formed with the second graft unit as one unitary body.

In accordance with one aspect of the invention, a spinal bone graft for implantation into a host can include one or more cortical bone portions forming a first unit. The first unit can include a first bone engagement surface for contacting a bone of the host, and a first mating surface opposite the first bone engagement surface. The first mating surface can form at least one first undercut. The spinal bone graft can also include one or more cortical bone portions forming a second unit. The second unit can include a second bone engagement surface for contacting a bone of the host, and a second mating surface opposite the second bone engagement surface. The second unit can also include at least one connector. The at least one connector can have a cross section, that includes a first end having one or more lateral projections. The at least one first undercut can have a cross section configured to mate with the cross section of the first end of the at least one connector to receive the first end of the at least one connector in an interlocking fit, to interconnect the first unit and the second unit together.

The at least one connector can be integrally formed with the second unit as one unitary body.

The at least one connector can include a second end opposite the first end, the second end having one or more lateral projections.

The second unit can include at least one second undercut to receive the second end of the at least one connector in an interlocking fit.

The at least one second undercut can have a cross section configured to mate with a cross section of the second end of the at least one connector.

The at least one first undercut and/or the at least one second undercut can be defined by a polygonal shape.

The polygonal shape can be one of a triangle, quadrilateral, pentagon, hexagon, heptagon, octagon, nonagon, decagon, rectangle, trapezoid, equilateral polygon, equiangular polygon, regular polygon, irregular polygon or rounded polygon.

The at least one first undercut and/or the at least one second undercut can be defined by an oblong shape.

The at least one first undercut and/or the at least one second undercut can be defined by a circular shape, oval shape or elliptical shape.

The at least one undercut of the first unit and the at least one undercut of the second unit can collectively form a socket when the first unit is interconnected with the second unit by the at least one connector.

The socket can include a cross section having an hourglass shape or a bowtie shape.

The socket can terminate at the anterior faces of the first unit and the second unit to allow insertion of the at least one connector between the first unit and the second unit from the anterior faces of the first unit and the second unit.

The socket can terminate at the posterior faces of the first unit and the second unit to allow insertion of the at least one connector between the first unit and the second unit from the posterior faces of the first unit and the second unit.

The socket can terminate at the anterior faces and the posterior faces of the first unit and the second unit so as to form a through-passage in the spinal bone graft.

The first unit and the second unit can be elongated.

The first unit and the second unit can each include an anterior face and a posterior face opposite the anterior face.

The first unit and the second unit can define a curved plane made up of points that are equidistant from points on the anterior face and the posterior face.

The at least one undercut of the first unit can extend normal to the curved plane.

The at least one undercut of the second unit can extend normal to the curved plane.

The first unit can define at least one first void extending between the first engagement surface and the first mating surface.

The second unit can define at least one second void extending between the second engagement surface and the second mating surface.

The at least one first void can terminate at the first engagement surface and at the first mating surface.

The at least one second void can terminate at the second engagement surface and the second mating surface.

The at least one first void and the at least one second void can be aligned with one another when the first unit and the second unit are interconnected so as to collectively form at least one single void that extends through the spinal bone graft.

The at least one single void can be adapted to receive allograft or autograft material.

The at least one single void can be adapted to receive at least one connecting element to interconnect the first unit and the second unit.

The spinal bone graft can include the at least one connecting element.

The at least one connecting element can include a dowel pin pressed through the first unit and the second unit.

The dowel pin can be made of cancellous bone or cortical bone.

The at least one first void can include at least two first voids.

The at least one second void can include at least two second voids.

Each of the at least two first voids can be aligned with one of the at least two second voids when the first unit and the second unit are interconnected, so as to collectively form at least two single voids.

Each of the at least two single voids can extend through the spinal bone graft.

The at least one connector can have an end face that is flush with the exterior surfaces on the first unit and the second unit.

The at least one connector can have an end face that is recessed inside a socket, forming an indent for engagement with a surgical instrument or clamping element.

The socket can have a bow tie shape.

The socket can have a flat side wall.

The first unit and/or second unit can have a modified surface for promoting bone ingrowth.

The at least one connector can have a modified surface for promoting bone ingrowth.

At least one of the one or more cortical bone portions of the first unit and one or more cortical bone portions of the second unit can include demineralized bone.

The at least one connector can be configured to mate with the first mating surface of the first unit.

The at least one connector can be configured to mate with the second mating surface of the second unit.

The at least one connector can be configured to mate with the first mating surface of the first unit and with the second mating surface of the second unit to interconnect the first unit and the second unit together.

The at least one connector can be configured to mate with the first mating surface of the first unit and with the second mating surface of the second unit to interconnect the first unit and the second unit together with the first mating surface in direct contact with the second mating surface, the at least one connector preventing separation of the first unit and the second unit in response to tensile force.

The first unit can have a first maximum height and the second unit can have a second maximum height.

The spinal bone graft can have a net maximum height equal to the sum of the first maximum height of the first unit and the second maximum height of the second unit when the first unit and the second unit are interconnected by the at least one connector.

In another embodiment, a spinal bone graft for implantation into a host can have one or more cortical bone portions forming a first unit. The first unit can include a first bone engagement surface for contacting a bone of the host, and a first mating surface opposite the first bone engagement surface. The first mating surface can form at least one first undercut. The spinal bone graft can also have one or more cortical bone portions forming a second unit, the second unit comprising a second bone engagement surface for contacting a bone of the host, and a second mating surface opposite the second bone engagement surface, the second mating surface forming at least one second undercut. The spinal bone graft can further have at least one connector having a cross section, the cross section having a first end, a second end and a middle portion between the first end and the second end. The first end of the at least one connector can include one or more lateral projections such that a width of the first end is greater than a maximum width of the middle portion. Likewise, the second end of the at least one connector can include one or more lateral projections such that a width of the second end is greater than the maximum width of the middle portion. The at least one first undercut can have a cross section configured to mate with the cross section of the at least one connector at the first end to receive the first end of the at least one connector in an interlocking fit. Similarly, the at least one second undercut can have a cross section configured to mate with the cross section of the at least one connector at the second end to receive the second end of the at least one connector in an interlocking fit. The at least one connector can be configured to mate with the at least one first undercut and the at least one second undercut to interconnect the first unit and the second unit together. The first mating surface can be in direct contact with the second mating surface. The at least one connector can prevent separation of the first unit and the second unit in response to tensile force.

In another embodiment, a spinal bone graft for implantation into a host includes one or more cortical bone portions forming a first unit. The first unit can include a first bone engagement surface for contacting a bone of the host, and a first mating surface opposite the first bone engagement surface. The first mating surface can form at least one undercut. The spinal bone graft can also include one or more cortical bone portions forming a second unit. The second unit can include a second bone engagement surface for contacting a bone of the host, and a second mating surface opposite the second bone engagement surface. The second mating surface can form at least one projection. The at least one projection can include a base end coextensive with the second mating surface, and a free end opposite the base end. The free end of the at least one projection can have one or more lateral projections. The at least one undercut can have a cross section configured to mate with the cross section of the at least one connector to receive the at least one connector in an interlocking fit. The at least one connector can be configured to mate with the at least one undercut to interconnect the first unit and the second unit together. The first mating surface can be in direct contact with the second mating surface. The at least one connector can prevent separation of the first unit and the second unit in response to tensile force.

Composite bone grafts in accordance with embodiments of the invention can include two or more distinct bone portions or units where the bone portions are connected. The bone portions are preferably self-locking, interlocking, and/or connected by at least one mechanical connector. One or more of the bone portions may be demineralized, and may also be continuous or discontinuous. The composite bone graft may include one or more textured surfaces, preferably including a plurality of closely spaced protrusions. The composite bone graft is useful for repairing bone defects caused by congenital anomaly, disease, or trauma, and is particularly useful for spinal fusions. The composite bone graft can be appropriately sized for any application and can be used to replace traditional non-bone prosthetic implants. The composite bone graft promotes the growth of patient bone at an implantation site by promoting osteoinductivity and cellularization, provides added stability and mechanical strength, and does not shift, extrude or rotate, after implantation.

Composite bone grafts in accordance with embodiments of the invention can be used for repairing bone defects caused by congenital anomaly, disease, or trauma, including for example, for restoring vertical support of the posterior and/or anterior column. The present composite bone grafts can be used as structural grafts placed in the spine from a lateral approach as interbody grafts. The bone grafts can be used to supplement autologous bone for spinal fusions in patients who lack sufficient host bone and to avoid significant donor site morbidity.

Composite bone grafts in accordance with embodiments of the invention can be used for applications normally suited for only non-bone prosthetic implants because the composite bone graft can be appropriately sized for any application and has adequate mechanical strength.

Composite bone grafts in accordance with embodiments of the invention can include a plurality of bone portions layered to form a graft unit, and one or more biocompatible connectors for holding together the graft unit.

Composite bone grafts in accordance with embodiments of the invention can include two or more distinct bone portions, and one or more biocompatible connectors, where the biocompatible connectors hold together the two or more bone portions to form the composite bone graft.

Composite bone grafts in accordance with embodiments of the invention can include a composite bone graft including two or more connected, distinct bone portions.

Composite bone grafts in accordance with embodiments of the invention can include a composite bone graft including three or more connected, distinct bone portions.

Composite bone grafts in accordance with embodiments of the invention can include a composite bone graft including three or more connected, distinct cortical bone portions.

Composite bone grafts in accordance with embodiments of the invention can include one or more horizontally disposed channels or recesses provided through the composite bone graft perpendicular to the interfaces of the bone portions.

Composite bone grafts in accordance with embodiments of the invention can include one or more vertically disposed channels or recesses provided through the composite bone graft parallel to the interfaces of the bone portions.

Composite bone grafts in accordance with embodiments of the invention can include one or more horizontally disposed channels and vertically disposed channels where the one or more channels includes one or more therapeutically beneficial substances.

Composite bone grafts in accordance with embodiments of the invention can include two or more connected bone portions, where the bone portions can include cortical bone and cancellous bone.

Composite bone grafts in accordance with embodiments of the invention can include a first bone portion, a second bone portion, a third bone portion, the first, second and third bone portions being disposed one on the other (i.e. layered) to form a graft unit, and one or more biocompatible connectors for holding together the graft unit.

Composite bone grafts in accordance with embodiments of the invention can include a first cortical bone portion, a second cortical bone portion, a cancellous bone portion disposed between the first cortical bone portion and the second cortical bone portion to form a graft unit, and one or more biocompatible connectors for holding together the graft unit.

Composite bone grafts in accordance with embodiments of the invention can include a first cortical bone portion, a second cortical bone portion provided on the first cortical bone portion to form a graft unit, and one or more biocompatible connectors for holding together the graft unit.

Composite bone grafts in accordance with embodiments of the invention can include a plurality of layered cortical bone portions forming a graft unit, and one or more biocompatible connectors for holding together the graft unit.

Composite bone grafts in accordance with embodiments of the invention can include a plurality of layered bone portions forming a graft unit, and one or more biocompatible connectors for holding together the graft unit.

Composite bone grafts in accordance with embodiments of the invention can include a first bone portion, a second bone portion provided on the first bone portion to form a graft unit, and one or more biocompatible connectors for holding together the graft unit.

Composite bone grafts in accordance with embodiments of the invention can include a plurality of distinct bone portions, where one or more of the bone portions are demineralized.

Composite bone grafts in accordance with embodiments of the invention can include a plurality of distinct bone portions, where one or more of the bone portions are continuous or discontinuous.

Composite bone grafts in accordance with embodiments of the invention can include a plurality of distinct bone portions where one or more of the bone portions include a discontinuous bone portion, the discontinuous bone portion including one or more therapeutically beneficial substances including but not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; ViviGen® brand cellular bone matrix; ViviGen Formable™ brand cellular bone matrix; Grafton® brand demineralized bone matrix produced by Osteotech; DynaGraft® brand demineralized bone matrix; demineralized cortical bone; demineralized cancellous bone; collagen including one or more growth factors including for example Novus™ brand growth factors produced by Stryker Biotech; collagen including demineralized bone including for example DynaGraft® brand demineralized bone matrix; cancellous bone; cortical bone; Opteform™ brand bone graft material produced by the University of Florida; Osteofil™ brand bone graft material produced by Regeneration Technologies, Inc. (RTI); and growth factors including for example, bone morphogenic protein, and transforming growth factor-β. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset® brand bone graft substitute produced by Wright Medical. Suitable pharmaceutically active agents include but are not limited to, for example, growth factors including for example bone growth factors including for example bone morphogenic protein, and transforming growth factor-β, chemotherapeutic agents, anti-inflammatory agents, and antibiotics.

Composite bone grafts in accordance with embodiments of the invention can include a first cortical bone portion, a second cortical bone portion, a cancellous bone portion disposed between the first cortical bone portion and the second cortical bone portion to form a graft unit, and one or more biocompatible connectors for holding together the graft unit, where the cancellous bone portion is demineralized and discontinuous.

Composite bone grafts in accordance with embodiments of the invention can include a first cortical bone portion, a second cortical bone portion, and a third cortical bone portion disposed between the first cortical bone portion and the second cortical bone portion to form a graft unit, and one or more biocompatible connectors for holding together the graft unit, where the third cortical bone portion is demineralized and discontinuous.

Composite bone grafts in accordance with embodiments of the invention can include a first cortical bone portion, and a second cortical bone portion disposed apart from each other, and forming a graft unit, and one or more biocompatible mechanical connectors for holding together the graft unit, where the first and second cortical bone portions are disposed separate from each other by the biocompatible mechanical connectors, thereby forming a substantially void central area.

Composite bone grafts in accordance with embodiments of the invention can include a substantially void central area, where the substantially void central area further includes one or more therapeutically beneficial substances including but not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; ViviGen® brand cellular bone matrix; ViviGen Formable™ brand cellular bone matrix; Grafton® brand demineralized bone matrix produced by Osteotech; DynaGraft® brand demineralized bone matrix; demineralized cortical bone; demineralized cancellous bone; collagen including one or more growth factors including for example Novus™ brand growth factors produced by Stryker Biotech; collagen including demineralized bone including for example DynaGraft® brand demineralized bone matrix; cancellous bone; cortical bone; Opteform™ brand bone graft material produced by the University of Florida; Osteofil™ brand bone graft material produced by Regeneration Technologies, Inc. (RTI); and growth factors including for example bone morphogenic protein, and transforming, growth factor-β. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset® brand bone graft substitute produced by Wright Medical. Suitable pharmaceutically active agents include but are not limited to, for example, growth factors including for example bone growth factors including for example bone morphogenic protein, and transforming growth factor-β; chemotherapeutic agents; anti-inflammatory agents; and antibiotics. The material may be in any suitable form including for example, in the form of a solid, sponge, paste, powder, and/or gel.

Composite bone grafts in accordance with embodiments of the invention can include biocompatible connectors that feature one or more mechanical biocompatible connectors.

In addition, or in the alternative, composite bone grafts in accordance with embodiments of the invention can include biocompatible connectors that feature one or more chemical biocompatible connectors.

Composite bone grafts in accordance with embodiments of the invention can include mechanical biocompatible connectors that feature one or more pins.

Composite bone grafts in accordance with embodiments of the invention can include chemical biocompatible connectors that feature a biocompatible adhesive.

Composite bone grafts in accordance with embodiments of the invention can include mechanical biocompatible connectors that include one or more of the following biocompatible materials: cortical bone; stainless steel; titanium; cobalt-chromium-molybdenum alloy; a bioceramic; a bioglass; a plastic of one or more of the following: nylon, polycarbonate, polypropylene, polyacetal, polyethylene, and polysulfone; and one or more bioabsorbable polymers.

Composite bone grafts in accordance with embodiments of the invention can include mechanical biocompatible connectors that include cortical bone.

Composite bone grafts in accordance with embodiments of the invention can include one or more pins that include one or more cortical bone pins.

Composite bone grafts in accordance with embodiments of the invention can include one or more through-holes configured to accommodate the one or more pins.

Composite bone grafts in accordance with embodiments of the invention can include through-holes that are disposed perpendicular to interfaces of bone portions forming the graft unit.

Composite bone grafts in accordance with embodiments of the invention can include through-holes that are disposed perpendicular to interfaces of for example, the first bone portion, the second bone portion, and the third bone portion, of the graft unit.

Composite bone grafts in accordance with embodiments of the invention can include one or more pins and one or more through-holes configured to provide an interference fit for holding together the graft unit.

Composite bone grafts in accordance with embodiments of the invention can include one or more through-holes and one or more pins that are round, and an inner diameter of a through-hole can be smaller than a diameter of a pin, to provide an interference fit between the through-hole and the pin.

Composite bone grafts in accordance with embodiments of the invention can include one or more cortical bone pins that include a plurality of vertical grooves provided on a surface thereof.

Composite bone grafts in accordance with embodiments of the invention can include one or more cortical bone pins with a roughened surface.

Composite bone grafts in accordance with embodiments of the invention can include one or more cortical bone pins that feature a slot extending from one end of the bone pin.

Composite bone grafts in accordance with embodiments of the invention can include one or more pins threaded to provide a threaded engagement with one or more through-holes.

Composite bone grafts in accordance with embodiments of the invention can include one or more threaded pins and one or more threaded through-holes to provide a threaded engagement between the one or more pins and the one or more through-holes.

Composite bone grafts in accordance with embodiments of the invention can include one or more pins and one or more through-holes configured to provide a slidable connection, for example, to provide a composite bone-graft including a substantially void central area.

Composite bone grafts in accordance with embodiments of the invention can include one or more pins having a cross-section that includes a shape selected from the group including the following: round, ovoid, square, rectangular, triangular, pentagon, hexagon, and trapezoidal.

Composite bone grafts in accordance with embodiments of the invention can include a plurality of plate-like cortical bone portions, the cortical bone portions layered to form a graft unit, the graft unit held together with one or more cortical bone pins.

Composite bone grafts in accordance with embodiments of the invention can be in the form of a cortical cylinder.

Composite bone grafts in accordance with embodiments of the invention can include a graft unit having one or more through-holes configured to accommodate one or more pins, the graft unit including two or more bone portions layered to form the graft unit, and one or more pins for holding together the graft unit.

Composite bone grafts in accordance with embodiments of the invention can include a graft unit having one or more through-holes configured to accommodate one or more pins, the graft unit including a first plate-like cortical bone, a second plate-like cortical bone, a plate-like cancellous bone disposed between the first plate-like cortical bone and the second plate-like cortical bone to form the graft unit, and one or more cortical bone pins for holding together the graft unit.

Composite bone grafts in accordance with embodiments of the invention can include a graft unit having one or more through-holes configured to accommodate one or more pins, the graft unit including a first plate-like bone, a second plate-like bone provided on the first plate-like bone to form the graft unit, and one or more bone pins for holding together the graft unit.

Composite bone grafts in accordance with embodiments of the invention can include a flattened curved wedge graft unit having one or more through-holes configured to accommodate one or more pins, the graft unit including two or more plate-like cortical bone portions layered to form the graft unit, and at least two bone pins for holding together the graft unit, where the graft unit includes a substantially centrally located through-hole. The diameter of the through-hole may be readily selected by one of ordinary skill in the art without undue experimentation depending upon the particular application; for example, the diameter of the through-hole may be from about 2.0 mm-4.0 mm; preferably 2.5 mm-3.0 mm; and more preferably 3.0 mm.

Composite bone grafts in accordance with embodiments of the invention can include one or more through-holes disposed perpendicular to interfaces of plate-like bones of the graft unit.

Composite bone grafts in accordance with embodiments of the invention can include or take the form of a parallelepiped; a parallel block; a square block; a trapezoid wedge; a cylinder; a tapered cylinder; a cervical wedge (flattened curved wedge); an ovoid wedge (anterior lumbar wedge graft) and a polyhedron.

Composite bone grafts in accordance with embodiments of the invention can include or take the form of a polyhedron including six planar surfaces.

Composite bone grafts in accordance with embodiments of the invention can include one or more textured surfaces.

Composite bone grafts in accordance with embodiments of the invention can include one or more textured surfaces with a plurality of closely spaced continuous protrusions.

Composite bone grafts in accordance with embodiments of the invention can include a cross-section having one or more shapes selected from the following: irregular; triangular, square, rectangular, and curved.

Composite bone grafts in accordance with embodiments of the invention can include a plurality of continuous protrusions sized to be in a range of greater than or equal to about 1.5 mm in length; about 0.5 to about 10.0 mm in width and about 0.1 to about 5.0 mm in depth.

Composite bone grafts in accordance with embodiments of the invention can include a plurality of closely spaced continuous protrusions spaced from about 0.0 to about 3.0 mm apart.

Composite bone grafts in accordance with embodiments of the invention can include a plurality of protrusions spaced from about 0.1 to about 2.0 mm apart.

Composite bone grafts in accordance with embodiments of the invention can include a plurality of protrusions spaced about 0.5 mm apart.

In other embodiments, a method for restoring vertical support of the posterior and/or anterior column includes the step of implanting a composite bone graft including two or more distinct bone portions held together by one or more connectors, at a site in a patient.

Composite bone grafts in accordance with embodiments of the invention can contain two or more connected bone portions, where the composite bone graft has a plurality of closely spaced protrusions on one or more surfaces thereof, where the protrusions are continuous protrusions, discrete protrusions, or a combination thereof.

Composite bone grafts in accordance with embodiments of the invention can include plate-like cortical and/or cancellous bone portions that are continuous bone portions and/or discontinuous bone portions.

Composite bone grafts in accordance with embodiments of the invention can include one or more discontinuous bone portions.

Composite bone grafts in accordance with embodiments of the invention can include one or more discontinuous, demineralized cortical bone portions.

Composite bone grafts in accordance with embodiments of the invention can include one or more discontinuous, demineralized cancellous bone portions.

Composite bone grafts in accordance with embodiments of the invention can include one or more continuous or discontinuous cancellous bone portions, (continuous or discontinuous and/or demineralized), one or more therapeutically beneficial substances including but not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; ViviGen® brand cellular bone matrix; ViviGen Formable™ brand cellular bone matrix; Grafton® brand demineralized bone matrix produced by Osteotech; DynaGraft® brand demineralized bone matrix; demineralized cortical bone; demineralized cancellous bone; collagen including one or more growth factors including for example Novus™ brand growth factors produced by Stryker Biotech; collagen including demineralized bone including for example DynaGraft® brand demineralized bone matrix; cancellous bone; cortical bone; Opteform™ brand bone graft material produced by the University of Florida; Osteofil™ brand bone graft material produced by Regeneration Technologies, Inc. (RTI); and growth factors including for example bone morphogenic protein, and transforming growth factor-β. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset® brand bone graft substitute produced by Wright Medical. Suitable pharmaceutically active agents include but are not limited to, for example, growth factors including for example bone growth factors including for example bone morphogenic protein, and transforming growth factory; chemotherapeutic agents; anti-inflammatory agents; and antibiotics.

Composite bone grafts in accordance with embodiments of the invention can include one or more continuous or discontinuous cancellous bone portions that are demineralized and include one or more therapeutically beneficial substances.

Composite bone grafts in accordance with embodiments of the invention can include one or more discontinuous cortical bone portions, and include one or more therapeutically beneficial substances.

Composite bone grafts in accordance with embodiments of the invention can include one or more discontinuous cortical bone portions that are demineralized, and include one or more therapeutically beneficial substances.

Composite bone grafts in accordance with embodiments of the invention can include two or more distinct bone portions held together by one or more connectors, where the composite-bone graft includes two diametrically opposing chamfered edges, one provided along the length of the graft at its top edge and the other provided along the length of the graft at its bottom edge, such that the chamfered edges are diametrically opposing.

Composite bone grafts in accordance with embodiments of the invention can include two or more distinct interlocking cortical bone portions.

Composite bone grafts in accordance with embodiments of the invention can include two or more distinct interlocking bone portions, where the interlocking bone portions are self-locking.

Composite bone grafts in accordance with embodiments of the invention can include two or more distinct interlocking bone portions, where the interlocking bone portions are locked with one or more locking pins.

Composite bone grafts in accordance with embodiments of the invention can include bone portions that are locked with one or more locking pins entirely or partially traversing a dimension of the composite bone graft.

Composite bone grafts in accordance with embodiments of the invention can include a bone graft where each complementary bone portion is provided with a discrete or continuous interlocking pattern.

Composite bone grafts in accordance with embodiments of the invention can include two or more distinct adjacent bone portions where adjacent bone portions are configured to interlock with each other, and one or more bone pins partially or entirely traversing a dimension of the graft, where the dimension of the graft is the length, width, or height of the graft.

Composite bone grafts in accordance with embodiments of the invention can include two or more distinct adjacent bone portions where adjacent bone portions are configured to interlock with each other.

Composite bone grafts in accordance with embodiments of the invention can include two or more distinct adjacent interlocking bone portions where adjacent bone portions include complementary peg-like protrusions and corresponding depressions, such that the protrusions and depressions provide an interlocking fit between the bone portions.

BRIEF DESCRIPTION OF THE DRAWINGS

The foregoing summary and the following detailed description will be better understood in conjunction with the drawing figures, which illustrate non-limiting examples, and of which.

DETAILED DESCRIPTION

Figure 1:
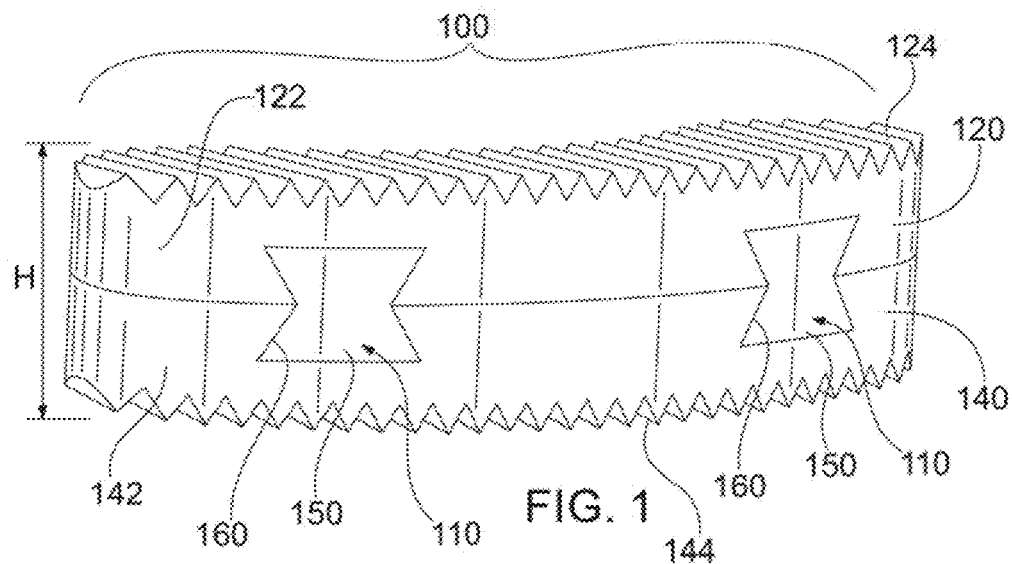
FIG. 1 is a perspective view of a bone graft in accordance with one embodiment of the invention.

Although the invention is illustrated and described herein with reference to specific embodiments, the invention is not intended to be limited to the details shown. Rather, various modifications may be made in the details within the scope and range of equivalents of the claims and without departing from the invention.

I. Definitions

The below definitions serve to provide a clear and consistent understanding of the specification and claims, including the scope to be given such terms to the extent that such terms are used, unless noted otherwise.

About. By the term "about" in reference to specific dimensions is intended to mean that the tolerance limits for overall or outer dimensions of the composite bone graft is plus or minus (+/−) 1.0 mm, and the tolerance limits for the width of individual cortical bone portions is plus or minus (+/−) 0.5 mm.

And/or. By the term "and/or", as used within a set of objects or things, is intended for the purposes of the present invention to mean at least one of the objects or things.

Bioabsorbable polymers. By the term "bioabsorbable polymers" is intended for the purposes of the present invention, bioabsorbable, bioabsorbable, biodegradable, and bioerodible materials that are well known to those of ordinary skill in the art and are described in Biomaterials Science—An Introduction to Materials in Medicine, edited by Ratner, B. D. et al., Academic Press, (1996), and include for example, the following materials: chitosan; isomorphic ploy (hexamethylene co-trans-1,4-cyclohexane dimethylene oxalates); poly(glycolic acid); copolymers of poly(glycolic acid) and poly(lactic acid); polydioxanone; poly(latic acid); polymers having a back-bone structure selected from the group consisting of: polyanhydrides, polyphophazenes, polyphosphonates, polyamides, and polyiminocarbonates; polyhydroxybutyrate; polyhydroxyvalerate; copolymers of polyhydroxybutyrate and polyhydroxyvalerate; polycaprolactone; polydioxanone; poly(.gamma.-ethyl glutamate); poly(DTH iminocarbonate); poly(Bisphenol A iminocarbonate); poly(DETOSU-1,6 HD-t-CDM ortho ester); poly(Sebacic acid-hexadecandioic acid anhydride); poly(ortho esters); poly(amino acids); and PLOA. Such polymers may optionally include one or more pharmaceutically active agents for controlled release applications, such agents including for example: osteoinductive factors including for example bone morphogenic protein; growth factors including for example transforming growth factor-β; chemotherapeutic agents; antiobiotics; and anti-inflammatory agents.

Biocompatible. By the term "biocompatible" is intended for the purposes of the present invention; any material which when implanted in a patient does not provoke an adverse response in the patient. A suitable biocompatible material when introduced into a patient is not toxic or injurious to that patient, or does not cause immunological rejection.

Biomechanical strength. By the term "biomechanical strength" is intended for the purposes of the present invention, those properties exhibited by a bone graft, including loading strength, compressive strength, and tensile strength.

Bone. By the term "bone" is intended for the purposes of the present invention, bone recovered from any source including animal and human, for example, human bone recovered for the production of allografts, and animal bone recovered for the production of xenografts, such allografts and xenografts suitable for implantation into a human. Such bone includes: any bone or portion thereof, including cut pieces of bone, including cortical and/or cancellous bone, for example, recovered from a human including a living human or a cadaver, or animal, and processed for implantation into a living patient. Such bones including for example: the humorous, hemi-pelvi, tibia, fibula, radius, ulna, rib, vertebrae, mandibular, femur, and ilia, and any cut portion thereof. Such bone may be demineralized or not demineralized. In a preferred embodiment a cancellous or cortical bone section is demineralized and disposed between two non-demineralized cortical bone portions. Suitable bone may also include continuous or discontinuous bone portions. For example, one or more bone portions of a composite bone graft may be discontinuous, for example, a bone portion may be perforated and demineralized, for example perforated either before or after demineralization, for example, to allow for uniform demineralization (perforations before demineralization) and to promote ingrowth of patient bone. Cancellous and/or demineralized cancellous and/or discontinuous cancellous and/or demineralized discontinuous cancellous and or discontinuous cortical and/or demineralized discontinuous cortical, bone, may optionally include one or more therapeutically beneficial substances provided with or without a carrier transforming growth factor-β; The composite bone graft may include a substantially void central area, where the substantially void central area further includes one or more therapeutically beneficial substances provided with or without a carrier. The material may be in any suitable form including for example, in the form of a solid, sponge, paste and/or gel.

Bone marrow elements. By the term "bone marrow elements" is intended for the purposes of the present invention, the highly cellular hematopoietic connective tissue filling the medullary cavities and spongy epiphysis of bones which may harbor bacterial and/or viral particles and/or fungal particles, and includes for example, blood and lipid.

Chamfer. By the term "chamfer" is intended for the purposes of the invention, an oblique face formed at a corner of a composite bone graft, at an angle to the adjacent principal faces. Suitable angles include angles in the range of from 38° to 52°, more preferably 40° to 50°, even more preferably 42° to 48°, and most preferably about 40° to 50°, even more preferably 42° to 48°, and most preferably about 45°.

Cleaned bone. By the term "cleaned bone" is intended for the purposes of the present invention, a bone or cut portion thereof, that has been processed using means known in the art, to remove bone marrow elements.

Closely Spaced. By the term "closely spaced" is intended for the purposes of the present invention, protrusions (discrete or continuous) which are in close proximity to each other. Preferably the protrusions are spaced no more than 3.0 mm apart (i.e. the distance between the edges of two adjacent protrusions), more preferably no more than 2.0 mm apart, even more preferably no more than 1.5 mm apart, and most preferably about 0.5 mm apart.

Coextensive. By the term "coextensive" is intended for the purposes of the present invention, a relationship between a first element and a second element in which the first element shares at least a portion of its boundary with the second element.

Composite. By the term "composite" is intended for the purposes of the present invention, a bone graft which is made up of two or more distinct bone portions.

Connector. By the term "connector" is intended for the purposes of the present invention, a means of connecting two or more distinct bone portions, including for example a chemical and/or mechanical means. By the term "mechanical connector" is intended for the purposes of the present invention, a structural member including for example, a pin. By the term "chemical connector" is intended for the purposes of the present invention, a biocompatible composition including for example, one or more biocompatible adhesives and one or more surface modification agents, and methods.

Continuous Bone Portion. By the term "continuous bone portion" is intended for the purposes of the present invention, a bone portion that is substantially solid without any-artificial void areas.

Continuous Protrusion. By the term "continuous protrusion" is intended for the purposes of the present invention, a protrusion whose length continues substantially uninterrupted, including for example a linear or curved protrusion whose length is at least three times greater than its width, preferably at least five times greater, and includes for example a continuous, protruding concentric ring, and a continuous linear protrusion, for example. Each continuous protrusion may or may not be distinct from another continuous protrusion.

Demineralized Bone. By the term "demineralized bone" is intended for the purposes of this invention, one or more distinct bone portions which have been demineralized by any method well known to those of ordinary skill in the art. Cortical bone is preferably demineralized in 0.5 to 0.6 N hydrochloric acid, or alternatively in 0.6 to 1.0 N hydrochloric acid, for a period of time of from about 1 to about 8 hours, more preferably for a time period of about two hours, at 25° C. to 50° C., more preferably at 25° C. to 37° C. Cancellous bone is preferably demineralized in 0.5 to 0.6N hydrochloric acid, or alternatively in 0.6 to 1.0 N hydrochloric acid, for a period of time of from about 20 minutes to about 6.0 hours, more preferably for a time period of from about 30 minutes to about 2.0 hours. Preferably, cortical and/or cancellous bone is demineralized to contain less than 10 wt % residual calcium, more preferably about less than 5 wt % residual calcium, even more preferably about 1 wt % to about 3 wt %, and most preferably about 2 wt % residual calcium. Other methods for demineralizing bone are well known in the art to which the present invention pertains, and can be readily selected and employed by one of ordinary skill in the art, without undue experimentation.

Discontinuous Bone Portion. By the term "discontinuous bone portion" is intended for the purposes of the present invention, a bone portion that contains artificially created void areas including for example, a perforated bone portion, where the perforations or channels may be of any shape and may partially or completely transverse the bone portion. Such perforations may be randomly disposed or disposed in a regular pattern on and/or through the bone portion. Suitable perforations include perforations traversing the width of the bone portion provided perpendicular to the interfaces of the bone portions of the composite graft, and channels traversing the height of the bone portion provided parallel to the interfaces of the bone portions of the composite graft. Such perforations allow for uniform demineralization of a bone portion, and allow for ingrowth of patient bone. A demineralized discontinuous bone portion may be perforated prior to demineralization or after demineralization.

Discrete Protrusion. By the term "discrete protrusion" is intended for the purposes of the present invention, a protrusion which is discontinuous, i.e. which has a distinct length and width, where each discrete protrusion is separate and distinct from every other discrete protrusion, and includes for example a protrusion whose length is less than three times its width, preferably less than twice its width and more preferably a protrusion whose length is about equal to its width.

Interlocking. By the term "interlocking" is intended for the purposes of the present invention, any pattern provided on a bone portion which allows that bone portion to engage or interlace with another bone portion, such that the engaged bone portions act as a single bone portion when stressed. Such bone portions may be provided with engaging patterns including but not limited to the following: step patterns, sawtooth patterns, and ridged patterns, patterns that define mortise and tenon joints, and lock and key type patterns. These patterns may be either discrete, for example one bone portion may include one or more protrusions and a complementary bone portion may be provided with one or more corresponding depressions, or continuous, for example bone portions are provided with complementary continuous grooves. The discrete patterns, may include protrusions and corresponding depressions of any shape and size sufficient to provide an interlocking fit, and include round, square, rectangular, triangular, oval, irregular, and any combination of geometric and curved shaped protrusions and corresponding depressions. The depth/height of the discrete or continuous patterns is from about 0.1 mm to about 3.5 mm, preferably from about 0.2 mm to about 2.0 mm, more preferably from about 0.3 mm to 1.5 mm, and most preferably from about 0.5 mm to about 1.0 mm. One of ordinary skill in the art to which the invention pertain can readily determine, select and employ an appropriate depth/height of the depression/protrusion based on the desired graft dimensions, whether or not a pin will also be used, clinical application, etc., without undue experimentation. Adjacent bone portions provided with interlocking patterns, may be self-locking such that no other connecting means, for example one or more pins, is necessary to form a unitary structure, i.e. to hold the composite bone graft together. Alternatively, interlocking bone portions may be "locked" to form a unitary structure using other connection means, for example, one or more pins partially or entirely traversing a dimension of the composite bone graft, where the dimension is for example the height, width, or length of the composite bone graft.

Load-bearing. By the term "load-bearing" is intended for the purposes of the present invention a non-demineralized bone product for implantation in a patient at a site where the bone graft will be expected to withstand some level of physical load(s).

Locking-pin. By the term "locking-pin" is intended for the purposes of the present invention, one or more pins entirely or partially traversing a dimension of a composite bone graft which serve to hold the bone graft together, for example, two or more interlocking bone portions provided with complementary patterns for example, a stepped pattern, may be locked using one or more pins, for example, one bone pin partially traversing the length of the graft.

Mechanical Strength. By the term "mechanical strength" is intended for the purposes of the present invention, the ability of a bone allograft to withstand mechanical loads at an implant site without failing.

Materials properties. By the term "materials properties" is intended for the purposes of the present invention, those properties present in normal fresh bone and include loading strength, compressive strength, tensile strength, and brittleness.

Normal bone. By the term "normal bone" is intended for the purposes of the present invention, fresh hydrated autogenous and/or fresh-frozen hydrated allograft bone tissue.

Osteoconductivity. By the term "osteoconductivity" is intended for the purposes of the present invention, the ability of a substance which by its presence conducts osteoinductive activity. Suitable osteoconductive materials include but are not limited to, for example, one or more biocompatible matrix materials. Suitable osteoconductive substances include but are not limited to, for example, hydroxyapitate; collagen; any biocompatible matrix material including for example, polymeric matrix materials, bioglass, bioceramics, resorbable Biomaterials, bioabsorbable polymers, a plastic matrix, stainless steel, titanium, and cobalt-chromium-molybdenum alloy matrix, and, substances including hydroxyapitate, including for example, Osteoset™ produced by Wright Medical.

Osteoinductivity. By the term "osteoinductivity" is intended for the purposes of the present invention, the ability of a substance to promote bone growth. Suitable osteoinductive substances include but are not limited to, for example, autograft bone; allograft bone; ViviGen® brand cellular bone matrix; ViviGen Formable™ brand cellular bone matrix; Grafton® brand demineralized bone matrix produced by Osteotech; DynaGraft® brand demineralized bone matrix; demineralized cortical bone; demineralized cancellous bone; collagen including one or more growth factors including for example Novus™ brand growth factors produced by Stryker Biotech; collagen including demineralized bone including for example DynaGraft® brand demineralized bone matrix; cancellous bone; cortical bone; Opteform™ brand bone graft material produced by the University of Florida; OsteoFil™ brand bone graft material produced by Regeneration Technologies, Inc. (RTI); growth factors including for example, bone morphogenic protein and transforming growth factor-β. Preferably, when a demineralized bone product is used the bone is demineralized to contain less than 6 wt % residual calcium, more preferably demineralized to contain 1 wt % to about 3 wt % residual calcium, and most preferably demineralized to contain about 2 wt % residual calcium.

Parallelepiped. By the term "parallelepiped" is intended for the purposes of the present invention, a six-faced polyhedron all of whose faces are parallelograms lying in pairs of parallel planes.

Polyhedron. By the term "polyhedron" is intended for the purposes of the present invention, a solid formed by plane faces, preferably formed by six faces.

Protrusion. By the term "protrusion" is intended for the purposes of the present invention, an irregularity in a surface of a bone allograft having a height of from 0.1 to 5.00 mm, preferably 0.3 to 3.0 mm, more preferably 0.5 to 1.5 mm, and most preferably 0.75 mm to 1.2 mm. The protrusions can be discrete, continuous, or a combination thereof, and can be of any shape including for example: irregular; pyramidal; conical; cuboidal; rectangular; and cylindrical; or any-combination thereof. Further, a cross-section of a continuous or discrete protrusion may be of any shape including for example: irregular; rectangular; square; oval; round; triangular; trapezoidal; and a regular or irregular curve; or any combination thereof. The protrusions can be provided on the bone allograft surface in a regular, symmetric pattern including for example a linear pattern or in an irregular pattern.

Self-locking, interlocking pattern. By the term "self-locking, interlocking pattern" is intended for the purposes of the present invention, any complementary patterns provided on adjacent bone portions which enable the bone portions: to interlock, act as a unitary structure, and the bone portions are held together, without the use of any additional connecting means.

Stability. By the term "stability" is intended for the purposes of the present invention the ability of the present composite bone graft to remain at an implantation site without significantly shifting, rotating, or being extruded.

Stress. By the term "stress" is intended for the purposes of the present invention, load per unit cross-sectional area.

Textured. By the term "textured" is intended for the purposes of the present invention, a composite bone graft having one or more textured surfaces provided on the surface of the composite bone graft where the surface of the composite bone graft can be any surface or a portion of any surface including a natural surface and/or a cut surface. The textured surface preferably includes a plurality of protrusions provided on the surface or a portion thereof, the protrusions of a shake including for example, irregular; pyramidal; conical; cuboidal; rectangular; trapezoidal: curved and cylindrical; or any combination thereof. The protrusions can be discrete, continuous, or a combination thereof.

Therapeutically Beneficial. By the term "therapeutically beneficial" is intended any material which by its action or presence, bring about a therapeutic result in a patient. Such materials include but are not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; ViviGen® brand cellular bone matrix; ViviGen Formable™ brand cellular bone matrix; Grafton® brand demineralized bone matrix produced by Osteotech;

DynaGraft® brand demineralized bone matrix; demineralized cortical bone; demineralized cancellous bone; collagen including one or more growth factors including for example Novus™ brand growth factors produced by Stryker Biotech; collage including demineralized bone including for example DynaGraft® brand demineralized bone matrix; cancellous bone; cortical bone; Opteform™ brand bone graft material produced by the University of Florida; OsteoFil™ brand bone graft material produced by Regeneration Technologies, Inc. (RTI); growth factors including for example bone morphogenic protein, and transforming growth factor-β. Suitable osteoconductive substances include but are not limited to, for example, hydroxyapitate; collagen; any biocompatible matrix material including for example, polymeric matrix materials, bioglass, bioceramics, resorbable Biomaterials; bioabsorbable polymers; a plastic matrix; stainless steel; titanium; cobalt-chromium-molybdenum alloy matrix; and substances including hydroxyapitate, including for example, Osteoset® brand bone graft substitute produced by Wright Medical. Suitable pharmaceutically active agents include but are not limited to, for example, growth factors including for example bone growth factors including for example bone morphogenic protein, and transforming growth factor-β, and transforming growth factor-β; chemotherapeutic agents; anti-inflammatory agents; and antibiotics.

Undercut. By the term "undercut" is intended a recess having any geometry that prevents an objected disposed in the recess from being withdrawn out of the recess in at least one direction. An example of such an undercut includes, but is not limited to, a dovetailed recess in a dovetailed joint.

II. Procurement and Preliminary Processing of Bone Tissue

Suitable bone tissue includes bone obtained from any animal or human source. Preferably, bone graft tissue can be obtained from the patient (autologous bone) or from a cadaver (allograft bone). When allograft bone tissue is used, it is processed under strict aseptic conditions in certified clean room operating suites. The bone tissue is preferably processed to remove all soft tissue, including marrow and blood, to produce a cleaned bone graft. Suitable processing methods are well known to those skilled in the art and can be readily selected and employed by those of ordinary skill in the art without undue experimentation. Suitable methods include the methods disclosed in, for example, U.S. Pat. Nos. 5,556,379; 5,820,581; and 5,797,891, the contents of which are incorporated by reference herein in their entireties.

After processing, the cleaned grafts are packaged under sterile conditions and stored for latter processing into the present composite bone allograft, or immediately processed into the present composite bone allograft followed by appropriate packaging. The use of fresh-frozen and/or freeze-dried, bone allografts are preferred.

III. How to Make a Preferred Embodiment of the Composite Bone Graft

Composite bone grafts in accordance with the invention can be manufactured using various techniques known in the art, including but not limited to the techniques described in U.S. Pat. No. 8,182,532, the content of which is incorporated by reference herein in its entirety.

IV. Detailed Description of Specific Embodiments of the Composite Bone Graft

Composite bone grafts in accordance with the invention can be appropriately sized for any application, and offer increased stability at an implant site to promote the ingrowth of patient bone, while providing excellent mechanical strength.

Referring to FIGS. 1-7, a composite spinal bone graft 100 is shown in accordance with a first embodiment of the invention. Bone graft 100 includes a first unit 120 and a second unit 140 interconnected with the first unit in a stacked arrangement. First unit 120 is formed of a cortical bone portion 122, and second unit 140 is formed of a cortical bone portion 142. It will be understood that composite bone grafts in accordance with the invention can feature more than two units. Moreover, it will be understood that composite bone grafts in accordance with the invention can feature units, where each unit is made up of more than one cortical bone portion. For example, a composite bone graft in accordance with the invention could include three or more units in a stacked arrangement, each unit made up of two or more cortical bone portions connected together. Any combination of units, and combination of cortical bone portions can be used.

Figure 2:
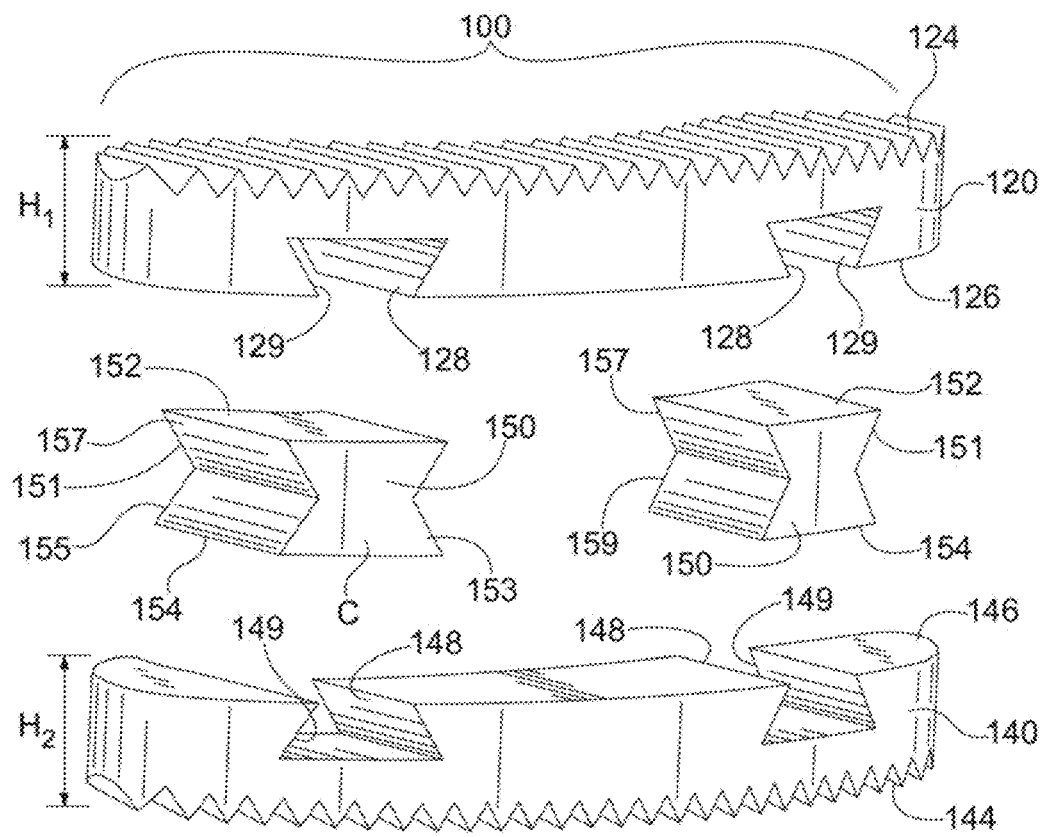
FIG. 2 is an exploded perspective view of the bone graft of FIG. 1.

Referring to FIGS. 1 and 2, first unit 120 includes a superior or upper surface in the form of a bone engagement surface 124 for contacting bone. First unit 120 also includes an inferior or lower surface in the form of a mating surface 126 opposite the bone engagement surface. Second unit 140 is shown oriented in a mirror arrangement of first unit 120. As such, second unit 140 includes an inferior or lower surface in the form of a bone engagement surface 144 for contacting bone. Second unit 140 also includes a superior or upper surface in the form of a mating surface 146 opposite bone engagement surface 144.

First unit 120 and second unit 140 are configured to interconnect with one another, with mating surface 126 in direct contact with mating surface 146. This interconnection, with direct engagement between the mating surfaces 126 and 146, minimizes the overall vertical profile or height H of bone graft 100, with the height being equal to the sum of the individual height dimension $H_1$ of first unit 120 and the individual height dimension $H_2$ of second unit 140.

Interconnection of first unit 120 and second unit 140 is facilitated by a low-profile, self-contained connection mechanism 110 that resides completely within the first and second units. As such, connection mechanism 110 does not increase either the footprint or the overall height H of bone graft 100. Connection mechanism 110 includes at least one connection feature on each of the first unit and the second unit, and at least one connector that cooperatively engages or mates with each of the connection features on the first and second units. The at least one connector can take one of several forms, and the connection features on each of the first unit 120 and second unit 140 can also take one of several forms.

Referring to FIG. 2, for example, connection mechanism 110 includes two connection features on first unit 120, two connection features on second unit 140, and two discrete connectors or keys 150 that engage with the connection features. Each connector 150 can be formed of natural bone material, such as an allograft or autograft, and can be of the same or different material(s) used to form the first unit 120 and the second unit 140.

The two connection features on first unit 120 are in the form of two recesses 128 defined in mating surface 126.

Similarly, the two connection features on second unit 140 are in the form of two recesses 148 defined in mating surface 146. Each connector 150 has a first end 152, a second end 154 opposite the first end, and a middle portion 156. In addition, each connector 150 has an elongated body 151 that terminates at a first end face 153 at one end, and terminates at a second end face 155 at the opposite end. The cross section C of each connector 150 remains uniform along and throughout the entire length of the connector, remaining constant as it progresses from first end face 153 to second end face 155.

Connectors in accordance with embodiments of the invention can have various cross-sectional shapes. In some embodiments, the connectors have a cross-sectional shape adapted to engage undercuts in the first and second units, so as to interconnect the first and second units together in an interlocking fit.

Figure 6:
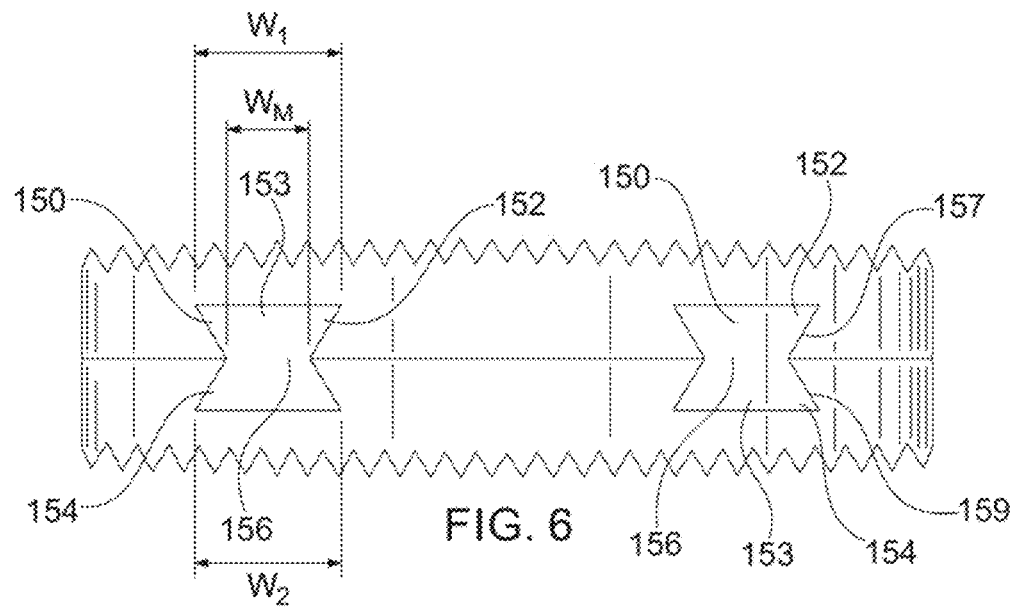
FIG. 6 is an elevation view of the anterior end of the bone graft of FIG. 1.

For example, each connector 150 has a first end 152 configured to engage one of the recesses 128 in first unit 120. Each connector 150 also has a second end 154 opposite first end 152, the second end being configured to engage one of the recesses 148 in second unit 140. Referring to FIG. 6, each first end 152 features one or more lateral projections, such that the width $W_1$ of the first end is greater than a maximum width $W_M$ of middle portion 156. Likewise, each second end 154 features one or more lateral projections, such that the width $W_2$ of the second end is greater than a maximum width $W_M$ of middle portion 156.

Each of recesses 128 is formed as an undercut 129. Similarly, each of recesses 148 is formed as an undercut 149. Undercuts 129 have cross sectional shapes that are substantially identical to the cross sectional shapes of first ends 152, and undercuts 149 have cross sectional shapes that are substantially identical to the cross sectional shapes of second ends 154. In this arrangement, each undercut 129 is adapted to receive a first end 152 of one of the connectors 150 in a longitudinal insertion direction parallel to the longitudinal axis of the undercut. Each undercut 149 is likewise adapted to receive a second end 154 of one of the connectors 150 in a longitudinal insertion direction parallel to the longitudinal axis of the undercut.

It will be understood that cross sectional shapes of undercuts in accordance with the invention need not be identical to, or substantially identical to, the cross sectional shapes of the corresponding connector ends. Cross sectional shapes of undercuts in accordance with the invention can be very different from the cross sectional shapes of the corresponding connector ends, so long as the cross sectional shapes of the undercuts are configured to mate with the cross sectional shapes of the corresponding connector ends.

The connectors 150 have sidewalls 157 that taper inwardly as they extend from the first ends toward the middle portion 156, and sidewalls 159 that taper inwardly as they extend from the second ends toward the middle portion. When a first end 152 of a connector 150 is inserted into a recess 128, and a second end 154 of the same connector is inserted into a recess 148, the tapered sidewalls 157 and 159 are seated against undercuts 129 and 149, respectively. In particular, tapered sidewalls 157 are seated in recess 128 where they bear against undercut 129, and sidewalls 159 are seated in recess 148 where they bear against undercut 149. The undercuts 129 and 149 prevent the connectors 150 from being withdrawn from either of the recesses in any direction transverse to the longitudinal insertion direction of the connectors.

The geometries of the connectors, recesses and undercuts are preferably identical or substantially identical. For example, connectors 150, recesses 128 and recesses 148 all incorporate trapezoidal geometries that are identical. That is, the cross sectional shape of each first end 152, each second end 154, each recess 128 and each recess 148 has three sides that confirm to the shape of a trapezoid. As such, connectors 150 mate with recesses 128 and 148 in a tight fit consistent with a dovetail joint. This tight connection prevents separation of the first unit 120 and the second unit 140 in response to tensile force applied to the assembly.

It will be understood that the geometries of the connectors and undercuts can have various shapes, and need not be trapezoidal in order to facilitate an interlocking connection between the first and second units. The connectors and undercuts can have any shape that facilitates an interlocking connection. For example, the connectors and/or undercuts can have a polygonal shape conforming to a triangle, quadrilateral, rectangle, pentagon, hexagon, heptagon, octagon, nonagon or decagon. The connectors and/or undercuts can also have a polygonal shape conforming to an equilateral polygon or an equiangular polygon. In addition, the connectors and/or undercuts can have a polygonal shape confirming to a regular polygon or an irregular polygon. Moreover, the connectors and/or undercuts can have a polygonal shape confirming to a rounded polygon. Alternatively, the connectors and/or undercuts can also have an oblong shape that may or may not be polygonal. The connectors and/or undercuts can also be defined by a circular shape, oval shape or elliptical shape. Lastly, the connectors and/or undercuts can have a compound shape that incorporates one or more of the previously described shapes in combination.

Figure 3:
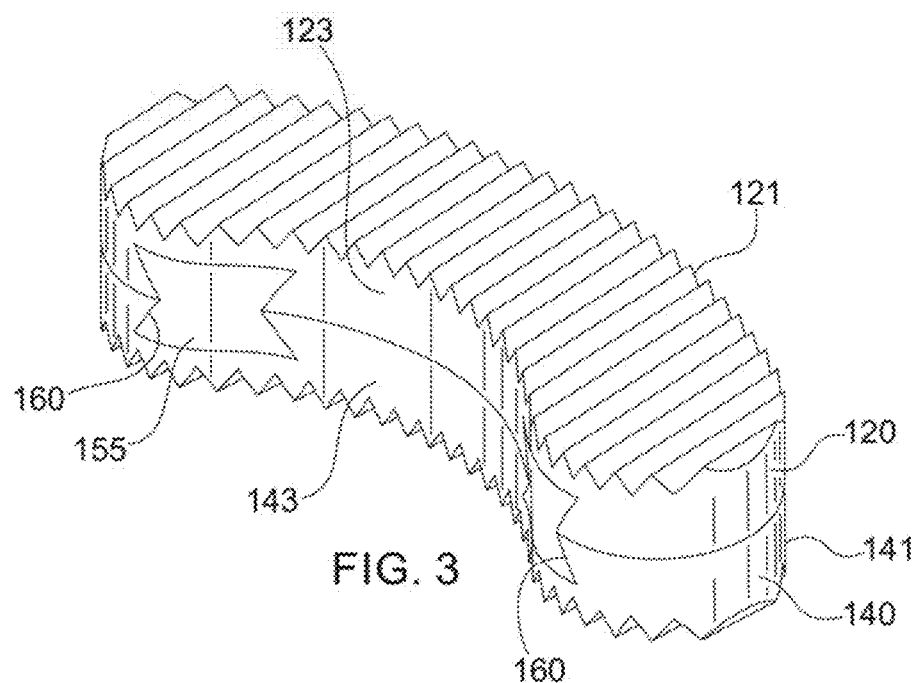
FIG. 3 is another perspective view of the bone graft of FIG. 1.
Figure 4:
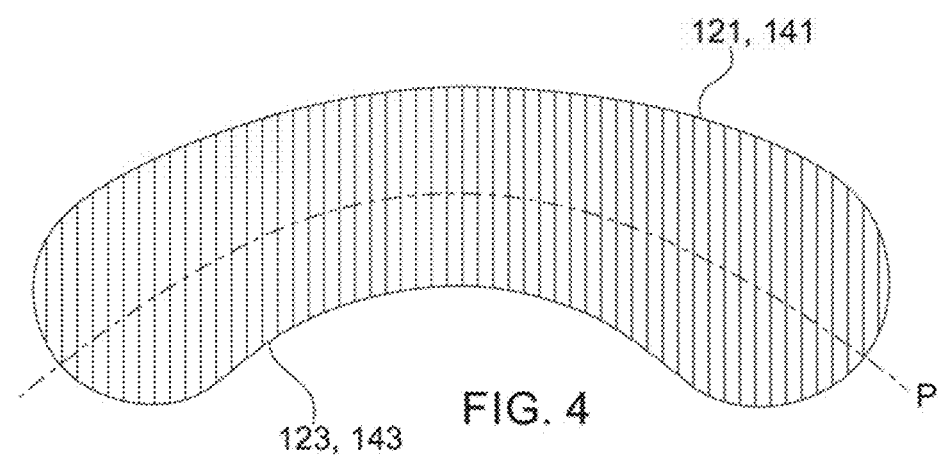
FIG. 4 is a top view of the bone graft of FIG. 1.

Referring to FIGS. 3 and 4, first unit 120 and second unit 140 are each elongated. In particular, first unit 120 includes an anterior elongated face 121 and an elongated posterior face 123 opposite the anterior face. Second unit 140 similarly includes an elongated anterior face 141 and an elongated posterior face 143 opposite the anterior face. First unit 120 is characterized by a curved plane P made up of points that are equidistant from points on anterior face 121 and posterior face 123. Likewise, second unit 140 is characterized by a curved plane P made up of points that are equidistant from points on anterior face 141 and posterior face 143. Each of undercuts 129 extends longitudinally in a direction normal to the curved plane P of first unit 120. Each of undercuts 149 similarly extends longitudinally in a direction normal to the curved plane P of second unit 140. Recesses and undercuts in accordance with embodiments of the invention can also extend transversely to curved plane P at various angular orientations. In addition, recesses and undercuts can extend tangentially to the curvature of plane P.

Each undercut 129 of first unit 120 vertically aligns with an undercut 149 on second unit when the first unit is interconnected with the second unit, as seen best in FIG. 1. In this arrangement, the vertically aligned undercuts 129 and 149 join with one another to form sockets 160, each socket having a perimeter entirely defined within and enclosed by first unit 120 and second unit 140. Sockets 160 have a "bow tie" or "butterfly" shape due to the trapezoidal geometries of the connectors 150, recesses 128 and recesses 148. It will be understood that because other recess geometries can be used, the shape of the sockets can also have or resemble other shapes, including but not limited to hourglass shapes, regular polygonal shapes, irregular polygonal shapes, or various other shapes that permit connectors to bear against the insides of the recesses to prevent separation of the first and second units in a direction transverse to the longitudinal insertion direction.

Bone grafts in accordance with embodiments of the invention can have sockets that extend partially through or completely through the grafts. For example, the sockets can terminate at an anterior face and/or a posterior face of the bone graft. Socket 160 terminates at the anterior faces 121, 141 of the first unit 120 and the second unit 140. This allows insertion of connectors 150 between the first unit 120 and the second unit 140 via the anterior faces 121, 141 of the first unit and the second unit. Socket 160 also terminates at the posterior faces 123, 143 of the first unit 120 and the second unit 140. This allows insertion of connectors 150 between the first unit 120 and the second unit 140 via the posterior faces 123, 143 of the first unit and the second unit. By terminating at both the anterior faces 121, 141 and posterior faces 123, 143, each socket 160 forms a through-passage in the spinal bone graft.

Bone grafts in accordance with embodiments of the invention can feature textured surfaces on the bone engagement surfaces to increase surface area and promote bone ingrowth. For example, the bone engagement surfaces can include surface roughening or etching. In addition, or in the alternative, the bone engagement surfaces can include one or more surface projections. Surface projections can be designed and arranged in a uniform pattern or non-uniform randomized pattern. Projections can take the form of linear projections, pyramidal projections, spikes, round projections, trapezoidal projections, or other protuberances. Linear projections can resemble ridges or teeth, which may be v-shaped or saw-tooth shaped. Referring to FIGS. 3 and 4, bone engagement surface 124 has a series of parallel v-shaped ridges or projections 129, and bone engagement surface 144 has a series of parallel v-shaped ridges or projections 149.

Bone grafts in accordance with the invention can have bone engagement surfaces with various degrees of slope or taper, so as to conform to surrounding bone surfaces. For example, the bone engagement of the superior or first graft unit can form a slope from the anterior face toward the posterior face, with the height of the first graft unit starting at a maximum height at the anterior face and tapering to a minimum height at the posterior face. The inferior or second graft unit can have the same slope or a different slope that also slopes from the anterior face toward the posterior face. The degree of slope can be at various angles, depending on the orientation of bone surfaces to be engaged by the bone engagement surfaces. For example, the angle of slope of each graft unit can range from about 0° to about 10°, and preferably from about 0° to about 7°.

The combined slopes of the first graft unit and second graft unit create a taper T. The degree of taper T can depend on the particular section of the spine. For example, it may be desirable to use a taper T of between about 6° and about 8° for bone grafts in the cervical spine, while using a taper T of between about 4° and about 5° for the lumbar spine. It will be understood that tapers outside of these ranges may also be suitable, and that the ranges expressed herein are neither preferred ranges nor the only ranges that are suitable.

Figure 5:
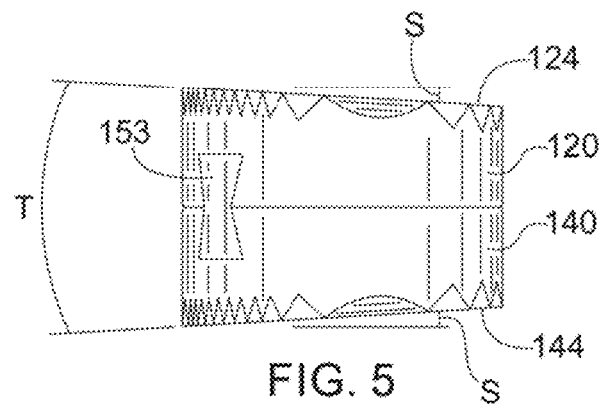
FIG. 5 is a side elevation view of the bone graft of FIG. 1, the opposite side being a mirror image.
Figure 7:
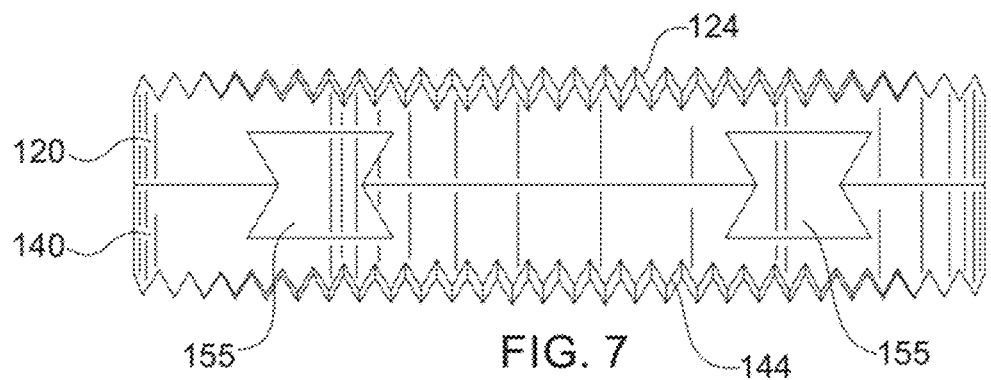
FIG. 7 is an elevation view of the posterior end of the bone graft of FIG. 1.

Referring to FIGS. 5-7, bone engagement surface 124 of first unit 120 and bone engagement surface 144 of second unit 140 are both sloped. In particular, bone engagement surface 124 has a slope S of 3.5° that tapers from anterior face 121 to posterior face 123. Likewise, bone engagement surface 144 has a slope S of 3.5° that tapers from anterior face 141 to posterior face 143. These combined slopes create a taper T of 7°, providing a wedge shape.

Figure 8:
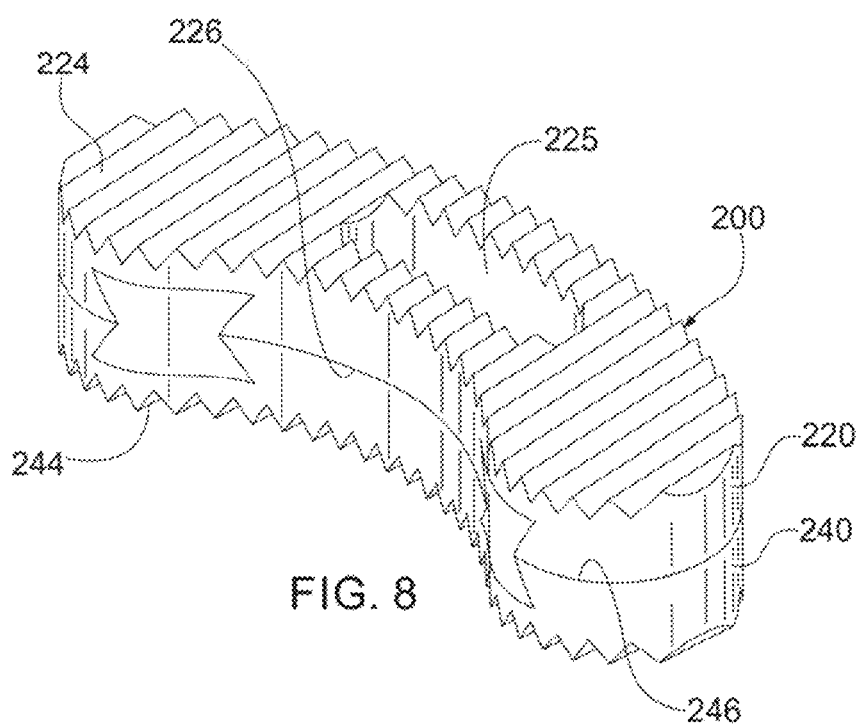
FIG. 8 is a perspective view of a bone graft in accordance with another embodiment of the invention.
Figure 9:
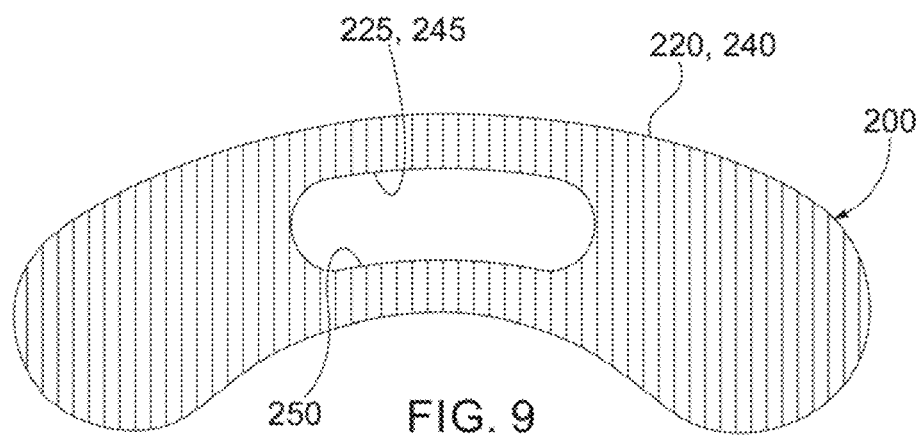
FIG. 9 is a top view of the bone graft of FIG. 8.

Referring to FIGS. 8 and 9, a spinal bone graft 200 is shown in accordance with another embodiment of the invention. Bone graft 200 has all of the same features as bone graft 100, and differs only with respect to a central void. For brevity, many features of bone graft 200 that are identical or similar to corresponding features of bone graft 100 will not be described.

A first unit 220 of bone graft 200 defines a first void 225 extending between a first engagement surface 224 and a first mating surface 226. A second unit 240 defines a second void 245 extending between a second engagement surface 244 and a second mating surface 246. The first void 225 terminates at the first engagement surface 224, and at the first mating surface 226. Similarly, the second void 245 terminates at the second engagement surface 244 and the second mating surface 246. The first void 225 and the second void 245 are aligned with one another when the first unit 220 and the second unit 240 are interconnected so as to collectively form a single void 250 that extends through the spinal bone graft. The single void 250 is adapted to receive allograft or autograft material.

Figure 10:
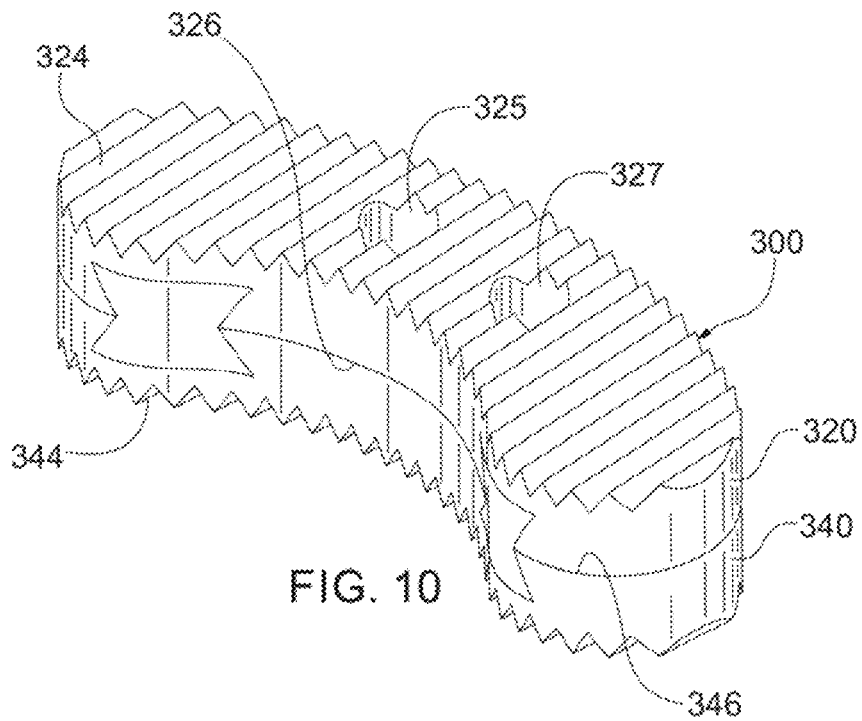
FIG. 10 is a perspective view of a bone graft in accordance with another embodiment of the invention.
Figure 11:
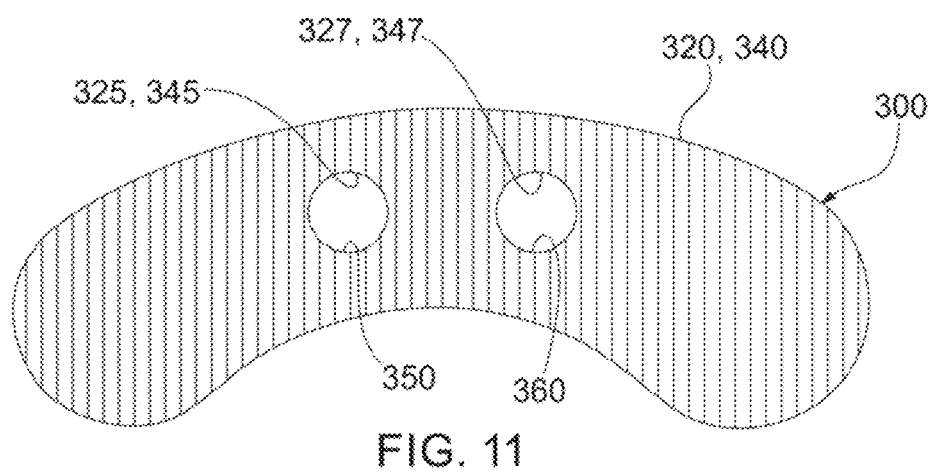
FIG. 11 is a top view of the bone graft of FIG. 10.

Referring to FIGS. 10 and 11, a spinal bone graft 300 is shown in accordance with another embodiment of the invention. Bone graft 300 has all of the same features as bone graft 100, and differs only with respect to two voids. For brevity, many features of bone graft 300 that are identical or similar to corresponding features of bone graft 100 will not be described.

A first unit 320 of bone graft 300 defines a first void 325 and a second void 327, each void extending between a first engagement surface 324 and a first mating surface 326. A second unit 340 defines a third void 345 and a fourth void 347 extending between a second engagement surface 344 and a second mating surface 346. The first void 325 and second void 327 terminate at the first engagement surface 324, and at the first mating surface 326. Similarly, the third void 345 and the fourth void 347 terminate at the second engagement surface 344 and the second mating surface 346. The first void 325 and the third void 345 are vertically aligned with one another when the first unit 320 and the second unit 340 are interconnected so as to collectively form a single void 350 that extends through the spinal bone graft. Similarly, the second void 327 and the fourth void 347 are vertically aligned with one another when the first unit 320 and the second unit 340 are interconnected so as to collectively form a single void 360 that extends through the spinal bone graft. Voids 350 and 360 are each adapted to receive a connecting element to interconnect the first unit 320 and the second unit 340. The connecting elements can include any type of connector for interconnecting bone graft units. In FIG. 8, the bone graft 300 is shown with a pair of dowel pins 370 that are configured to be pressed through the first unit 320 and the second unit 340. Each dowel pin 370 can be formed of cancellous bone or cortical bone.

Thus far, the connectors that interconnect the first and second graft units, such as connector 150, have been shown with end faces that terminate at ends of their respective sockets, such that the end faces of the connectors are flush or contiguous with the surrounding surfaces of the anterior and posterior faces. In these embodiments, the length of each connector is equal to the length of its respective socket. It may be desirable in some instances to have the length of each connector shorter than the length of its respective socket, so that both end faces of the connector are recessed in the socket, leaving small pockets or indents at each end of the socket. These pockets or indents can be utilized as engagement mechanisms for tools. In particular, the indents can be engaged or clamped onto by insertion tools. This avoids the need to mill special tool engagement features on the perimeter of the bone graft units.

Figure 12:
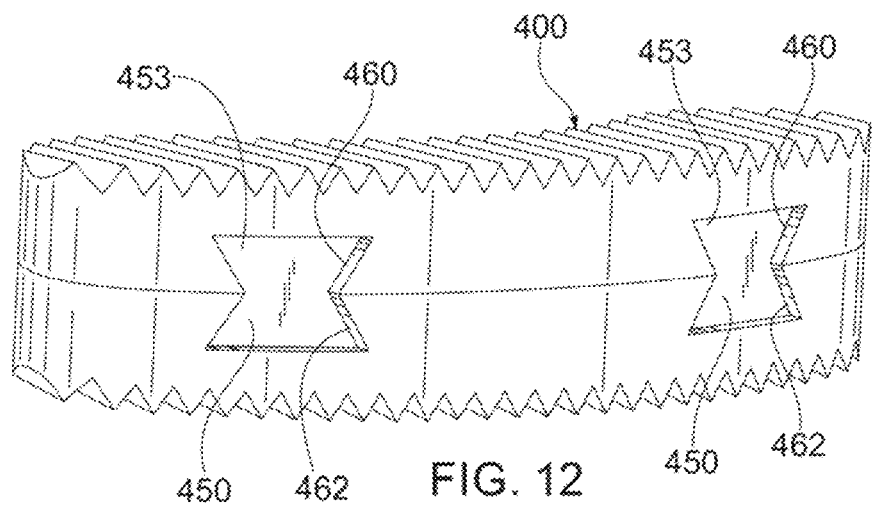
FIG. 12 is a perspective view of a bone graft in accordance with another embodiment of the invention using tapered connectors.

Referring to FIG. 12, a composite bone graft 400 is shown in accordance with another embodiment. Composite bone graft 400 has many of the same features as bone graft 100. For brevity, identical or similar features will not be described. Bone graft 400 includes a pair of connectors 450 that are positioned in respective sockets 460. Each connector 450 has a length that is shorter than the length of its respective socket 460, so that each end face of the connector terminates, or is recessed, inside the socket. The recessed end faces leave an indent 462 at the opening of each socket. FIG. 12 shows two indents 462 on the anterior side of the implant. Indents 462 are also present where the sockets exit on the posterior side of the implant. These indents 462 provide engagement surfaces that insertion tools and other instruments can clamp onto to manipulate the bone graft.

Figure 13A:
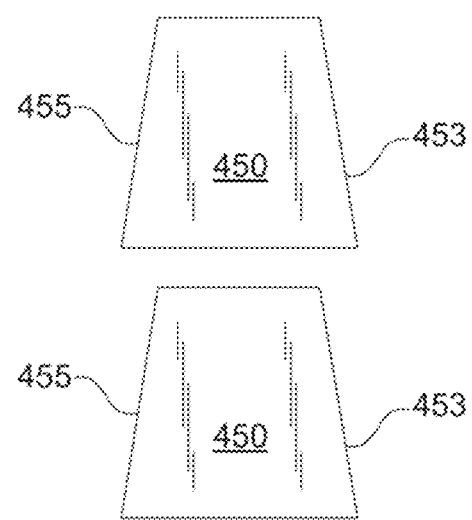
FIG. 13A is a top elevation view of the tapered connectors used in the bone graft of FIG. 12.
Figure 13B:
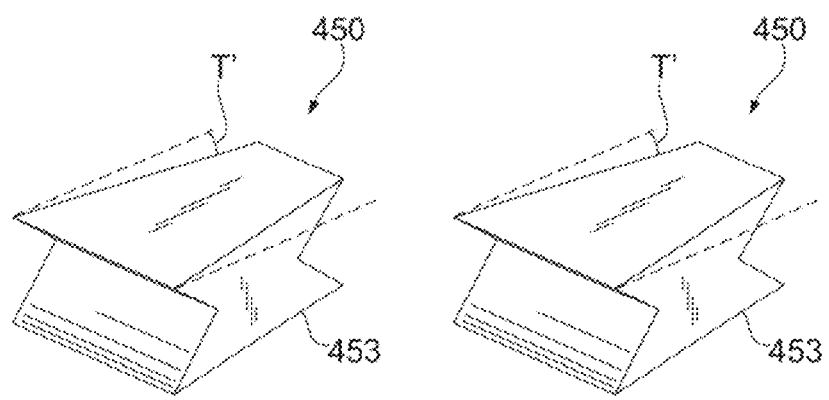
FIG. 13B is a perspective view of the tapered connectors used in the bone graft of FIG. 12.

The end faces of recessed connectors can have a surface geometry that is parallel to or otherwise conforms to the surfaces surrounding their respective sockets. Alternatively, the end faces of recessed connectors in accordance with the invention can have a non-conforming surface geometry that enhances engagement with an insertion tool. For example, end faces may include a slope or taper that forms an inner wall in each indent. The sloped inner wall can be configured to enhance retention of a gripping or clamping arm on an insertion tool. Referring to FIGS. 13A and 13B, for example, connectors 450 have end faces 453 and 455 that are tapered or sloped at an angle T' with respect to a plane encompassing the ends of their respective sockets. In this configuration, each connector 450 has a wider thickness at one end that tapers to a narrower thickness at the other end. When the connectors 450 are in the sockets 460, each recess is deeper at the end corresponding to the end of the connector having the narrower thickness. Sloped end faces 453 and 455 provide ramps inside the indents that facilitate a secure engagement with clamping arms on an insertion tool.

Bone grafts in accordance with the invention can be implanted with other materials to fill void space, such as demineralized bone matrix (DBM) putty or other void filling materials. These materials can often be placed adjacent to the posterior-facing side of the bone graft. Therefore, it may be desirable in some instances to prepare the posterior surfaces of the bone graft with one or more surface modifications or surface preparations to enhance fusion with the adjacent materials. The posterior faces of each graft unit can have prepared surfaces to enhance fusion. In addition, the end faces of each connector can also be prepared to enhance fusion. Surfaces on the posterior faces and/or end faces of the connectors can feature protrusions with geometries as described in other sections herein. In addition, or in the alternative, surfaces on the posterior faces and/or end faces of the connectors can feature etching or roughening to enhance fusion.

Figure 14:
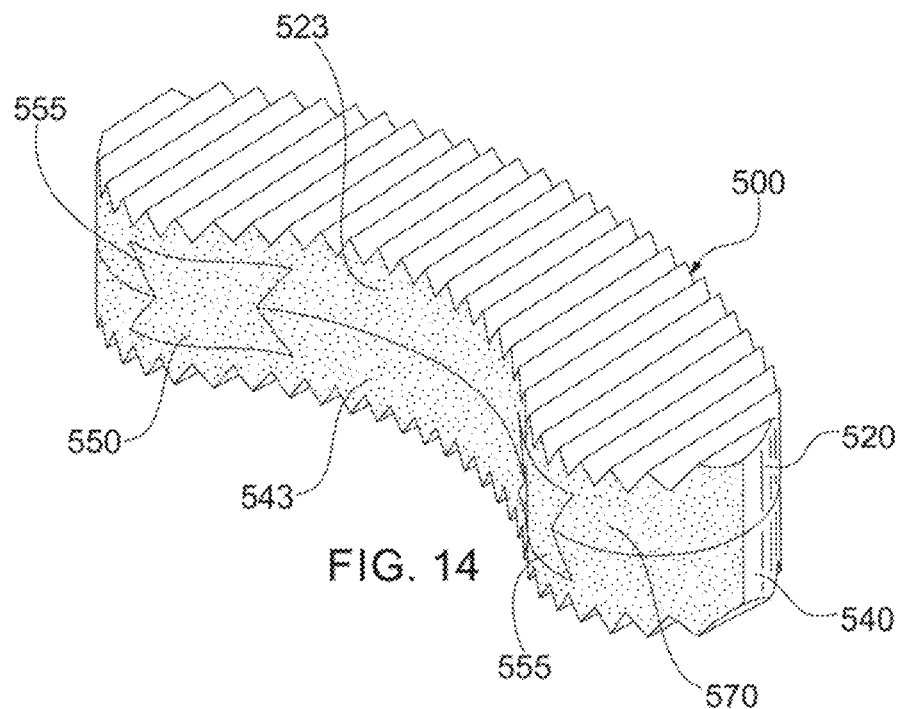
FIG. 14 is a perspective view of a bone graft in accordance with another embodiment of the invention.

Referring to FIG. 14, a composite bone graft 500 is shown in accordance with another embodiment. Composite bone graft 500 has many of the same features as bone graft 100. For brevity, identical or similar features will not be described. Bone graft 500 includes a first unit 520, a second unit 540 and connectors 550 with surface modifications to enhance fusion. In particular, the posterior face 523 of first unit 520, the posterior face 543 of second unit 540, and the posterior facing end faces 555 all have surface roughening 570 to enhance fusion with DBM putty or other void filling materials.

Figure 15:
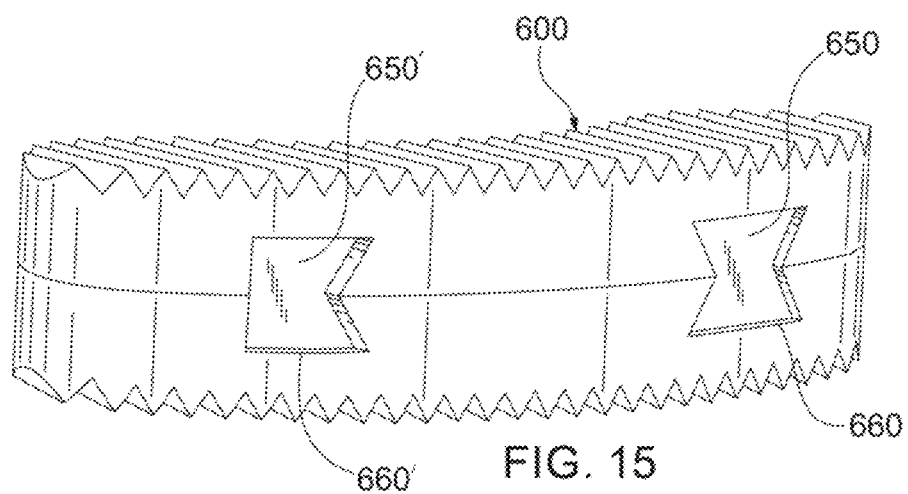
FIG. 15 is a perspective view of a bone graft in accordance with another embodiment of the invention.

Referring to FIG. 15, a composite bone graft 600 is shown in accordance with another embodiment. Composite bone graft 600 has many of the same features as bone graft 100. For brevity, identical or similar features will not be described. Bone graft 600 features a modified connector 650' and corresponding socket 660' on one side. On the opposite side, bone graft 600 has a bow tie shaped connector 650 and corresponding socket 660 that are similar to connectors and sockets in previously described embodiments. Connectors 650 and 650' are both recessed in sockets 660 and 660', respectively, forming indents that can receive clamping arms on insertion tools or other instruments. Modified connector 650' and socket 660' have a flat sidewall on one side as shown, as opposed to trapezoidal sides. The flat sidewalls can provide a better engagement with clamping tools and instruments that utilize flat clamping surfaces. Because they are flat, the flat sidewalls can provide a contour that is easier to clamp onto with commercially available insertion instruments, particularly instruments that feature clamping arms with flat clamping surfaces.

Bone grafts and connectors in accordance with embodiments of the invention can various dimensions, depending on the patient's condition and other factors. For example, suitable dimensions for the bone graft include a length of about 28 mm to about 32 mm, a width of about 10 mm to about 12 mm, and a height of about 7 mm to about 15 mm. Where a bow tie shaped connector is used, such as connector 150 shown in FIGS. 1-7, suitable dimensions for the connector include a length of about 11 mm to about 13 mm, a width of about 4 mm to about 6 mm, and a height of about 3 mm to about 5 mm.

Connectors in accordance with embodiments of the invention, including but not limited to the bow tie shaped connectors 150, can be used in various graft assemblies, including but limited to TLIF grafts. In addition, bone graft units and connectors in accordance with the embodiments of the invention that utilize indentations to accommodate instruments can also be used in various graft assemblies, including but limited to TLIF grafts.

Surface roughening can be used on all areas of bone grafts in accordance with different embodiments of the invention, including but not limited to the anterior side, posterior side, lateral sides, superior side, and/or interior side. Surface roughening as described herein can be used on various graft assemblies, including but limited to TLIF grafts, and the surface roughening can be produced using a variety of techniques in accordance with embodiments of the invention.

In embodiments that utilize one or more pins or dowels through the graft, such as the types of dowels shown in FIG. 10, the pins or dowels can be formed as cancellous bone plugs. In addition, the pins and dowels can be placed vertically, as shown in FIG. 10, or horizontally, i.e. in a direction within the plane perpendicular to the vertical direction shown in FIG. 10. In either direction, the pins, dowels or plugs promote fusion with surrounding materials.

Embodiments that include dowels or bone pins can include dowels or pins of various sizes. The diameter of each bone pin or dowel may be the same or different depending on the particular application, implant and size of the graft. For example, the diameter can be about 1.0 to about 5.0 mm, more preferably from about 1.5 mm to about 4.0 mm, even more preferably from about 2.0 to about 3.5 mm, and most preferably 2.5 to 3.0 mm.

Composite bone grafts in accordance with embodiments of the invention can include two or more bone portions, including any combination of cancellous and cortical bone portions, or cancellous or cortical bone portions alone, where the bone portions may optionally be demineralized, and may optionally be discontinuous, where the bone portions are connected, for example by interlocking the bone portions and/or by one or more mechanical and/or chemical connectors. Any cancellous bone portion and/or discontinuous bone portion (cortical and/or cancellous), and/or any demineralized bone portion (cortical and/or cancellous) may optionally include one or more pharmaceutically active agents or therapeutically beneficial substances provided therein, for example provided in the matrix of cancellous bone, or provided in any artificially created void areas. Both the cortical and cancellous bone portions may be solid and continuous or may be discontinuous (i.e. include one or more "holes" or "perforations" of any shape disposed at regular or random intervals throughout the bone portion. Bone portions may be provided with a pattern to enable an interlocking fit between cortical bone portions.

Suitable mechanical connectors include pin-type structures having any cross-section shape, such shapes including for example, round, square, triangular, rectangular, hexagon, pentagon, oval, irregular, and other geometries described elsewhere herein. The pin-type structure can include surface modification, for example the surface can be roughened, or provided with a plurality of horizontally or vertically disposed grooves (horizontal or vertically relative to the length of the pin); horizontally or vertically disposed ridges; or helical threads. The pin or surface-modified pin can also include one or more slots extending partially or entirely through the diameter of the pin, and extending partially or entirely through the length of the pin, suitable slots include for example, a slot extending partially through the diameter of the pin, for example about half-way through the diameter of the pin, and through the entire length of the pin; and a slot extending entirely through the diameter of the pin, and extending through a partial length of the pin for example, extending at least half-way through the length of the pin, preferably extending no more than about seven-eighths the length of the pin. Suitable mechanical connectors also include cotter pins. A composite graft can be pinned with one or more biocompatible pins, where the pins have substantially the same diameter or have a diameter different from each other. Suitable diameters can be readily selected and employed by one of ordinary skill in the art to which the present invention pertains without undue experimentation depending upon, for example, the particular application and implantation site, and the size and shape of the composite graft. The composite graft can be pinned with one or more biocompatible pins, entirely or partially traversing a dimension of the graft, for example, the height, length, and/or width of the composite graft. One of ordinary skill in the art to which the present invention pertains can readily select an appropriate pin, number of pins, and determine the orientation of the pin or pins, based on for example, the particular graft, whether the graft is interlocking or not, the orientation of the graft in the body, and the clinical indication, without undue experimentation.

Suitable chemical connectors include any biocompatible adhesive. Such adhesives are well known to those of ordinary skill in the art to which the present invention pertains, and can be readily selected and employed by those of ordinary skill in the art, without undue experimentation. Suitable chemical connectors also include known methods of biochemical surface modification. Such methods are well known to those of ordinary skill in the art to which the present invention pertains, and can be readily selected and employed by those of ordinary skill in the art, without undue experimentation.

The chemical and/or mechanical connectors may be used alone or in any combination and may include one or more therapeutically beneficial substances including for example, one or more osteoinductive substances, one or more osteoconductive substances and one or more pharmaceutically active agents.

Through-holes of a composite bone graft may also include surface modification. For example, if a threaded cortical bone pin is used, the through-hole or holes can optionally be threaded. The through-hole(s) can traverse any dimension of the graft, provided that they are placed such that when graft unit is connected the graft is held together. One of ordinary skill in the art to which the present invention pertains can readily select an optimum location for the through-holes based on criteria including the following: the anterior and posterior height of the composite bone graft, and the diameter of the mechanical and/or mechanical and chemical connectors, and the height of the protrusions. For example, when the anterior height is relatively small (i.e. 7.0 mm) and the diameter of the pin is relatively large (i.e. 2.5-3.0 mm), the through-holes can be spaced equidistant along the length of the graft unit, or displaced toward the posterior end of the graft unit.

The graft unit can be connected with one or more mechanical connectors. Suitable connections include any connection which is adequate to hold the bone portions of the graft unit together. Such connections include, for example, an interference or friction connection where the diameter of the pin is the same as or slightly larger than (preferably no more than 1.5 mm larger than the diameter of the through-hole) the diameter of the corresponding through-hole; a slidable connection where the diameter of the pin is the slightly less than the diameter of the through-hole, and a compression fit, where the pin is configured to allow compression upon insertion where the pin expands after insertion, achieved for example, by providing the pin with a slot.

Mechanical connectors can include pin-like connectors composed of any biocompatible material sufficient to hold together the present graft unit. Suitable biocompatible materials include for example, cortical bone; stainless steel; titanium cobalt-chromium-molybdenum alloy; and a plastic for example, of one or more of the following: nylon, polycarbonate, polypropylene, polyacetal, polyethylene, and polysulfone, where the plastic can optionally include fibers; and a polymer including one or more bioabsorbable polymaths including resorbable calcium phosphates; bioceramics and/or glasses including for example bioactive glasses and glass-ceramics; and calcium phosphate ceramics. Such mechanical connectors including for example, bioabsorbable polymers may optionally include one or more active agents, including for example one or more pharmaceutically active agents and/or one or more therapeutically beneficial agents, provided on the surface or impregnated in the matrix of the material.

The surface of the mechanical connector can be modified by methods well known to those of ordinary skill in the art to which the invention pertains, and include for example the following: (a) modification to influence cell adhesion and growth, provided by: (I) oxidized polystyrene surface, (ii) ammonia plasma-treated surface, and (iii) plasma-deposited acetone or methanol film, (b) modification to control protein adsorption; and (c) modification to improve lubricity.

Composite bone grafts can have a shape including, for example, a square; rectangular or curved block; a flattened curved wedge (i.e. a cervical wedge for use in cervical fusion); a wedge; a trapezoid wedge; a polyhedron block, a parallelepiped; a cylinder or dowel having a uniform diameter or a decreasing or increasing diameter, for example a tapered cylinder or tapered dowel; a dowel or tapered dowel having a cross-section of a shape including for example, round, oval, square, rectangular, triangular, pentagon, or hexagon.

Composite bone grafts can include one or more partially or completely textured surfaces. Preferably, a textured composite bone graft includes opposing textured surfaces disposed perpendicular to the interface(s) of the bone portions. The textured surface of the composite bone graft includes a plurality of protrusions. The protrusions can be formed over an entire surface of the composite bone graft or over a portion of a surface, for example over the entire cut surfaces, or over a portion of the cut surfaces. The plurality of protrusions can be formed on the surface in any number of ways well known to those of ordinary skill in the art to which the present invention pertains, including for example mechanical and/or chemical methods, including for example, by forming a series of parallel linear or curved grooves. The bone allograft protrusions can be formed by milling, for example by milling a set of parallel linear groves to form a saw-tooth configuration on the cut surface of the composite graft to form continuous linear protrusions; by milling a first set of parallel linear groves followed by turning the graft and forming a second set of parallel grooves at an angle to the first series, for example, at a 90° angle to form a plurality of discrete pyramidal protrusions. Milling is preferably achieved, by for example: running the graft over a milling tool which includes a plurality of closely spaced blades which can be adjusted to achieve a desired height and width; to form the discrete pyramidal protrusions, the graft can then be turned at, for example, a 90° angle and again run over the milling tool to produce the discrete protrusions illustrated. Milling can also be achieved using for example a routing or dremel tool, a laser, and masking and acid etching.

Other protrusions, for example concentric rings or other curved or irregular, of regular protrusions can be provided by attaching a drill bit having a blade corresponding to the protrusion pattern desired where the blade is appropriately sized to provide a desired protrusion width; length, and height, to a drill and drilling the desired surface of the bone to achieve the desired textured surface. One of ordinary skill in the art can readily design and produce, or select, and employ an appropriate milling tool to achieve a desired textured surface on a bone allograft, without undue experimentation.

Preferably, the protrusions (discrete, continuous, or a combination thereof) present on one or more surfaces of the present allograft are closely spaced, preferably from about 0.0 to 3.0 mm apart, preferably 0.1 to 2.0 mm apart, more preferably about 0.2 to 1.5 mm apart, and most preferably about 0.5 mm apart, (that is, there is preferably a distance of from 0.0 to 3.0 mm between the edges of two adjacent protrusions). The protrusions preferably have a height of from 0.1 to 5.00 mm, preferably 0.3 to 3.0 mm, more preferably 0.5 to 1.5 mm, and even more preferably 0.75 mm to 1.3 mm, and most preferably about 1.2 mm.

Composite bone grafts can include one or more void areas. Examples of such grafts include a composite graft having for example a first and a second cortical bone portion where the bone portions are for example slidably connected with for example one or more bone pins, where the first and second bone portion are disposed apart thereby creating a centrally located void. The void may optionally include any pharmaceutically active agent and/or therapeutically beneficial agent, including for example, osteoinductive substances including for example, bone morphogenic protein, hydroxyapitate, demineralized bone and bone products including for example ViviGen® brand cellular bone matrix; ViviGen Formable™ brand cellular bone matrix; Grafton® brand demineralized bone matrix and DynaGraft® brand demineralized bone matrix, and autograft bone; such substances may be in any form including for example, in the form of a paste, gel, or sponge.

As described earlier, the geometries of the connectors and undercuts can have various shapes, and need not be trapezoidal in order to facilitate an interlocking connection between the first and second units. The connectors and undercuts can have any shape that facilitates an interlocking connection. For example, the connectors and/or undercuts can have a polygonal shape conforming to a triangle, quadrilateral, rectangle, pentagon, hexagon, heptagon, octagon, nonagon or decagon. The connectors and/or undercuts can also have a polygonal shape conforming to an equilateral polygon or an equiangular polygon. In addition, the connectors and/or undercuts can have a polygonal shape confirming to a regular polygon or an irregular polygon. Moreover, the connectors and/or undercuts can have a polygonal shape confirming to a rounded polygon. Alternatively, the connectors and/or undercuts can also have an oblong shape that may or may not be polygonal. The connectors and/or undercuts can also be defined by a circular shape, oval shape or elliptical shape. Lastly, the connectors and/or undercuts can have a compound shape that incorporates one or more of the previously described shapes in combination.

Figure 16:
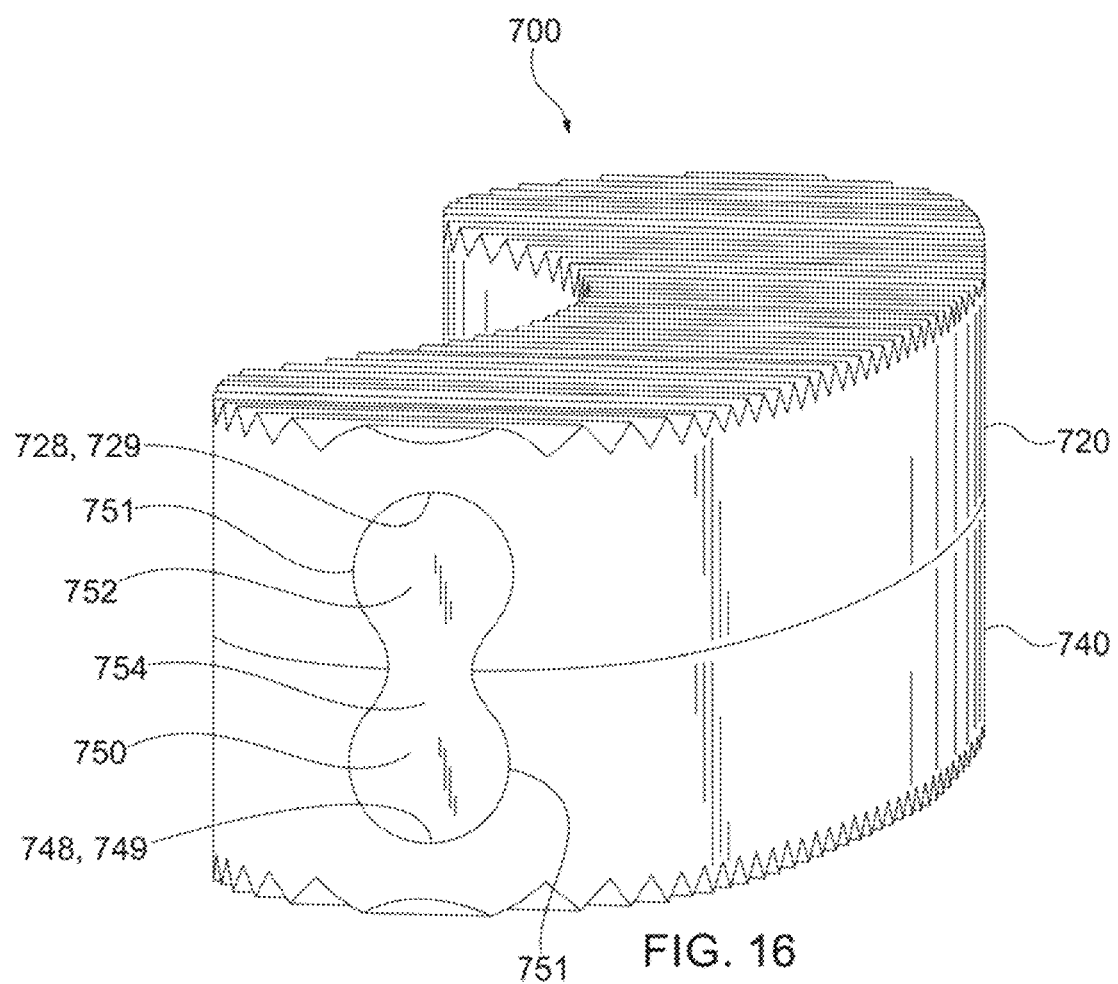
FIG. 16 is a perspective view of a bone graft in accordance with another embodiment of the invention.

For example, FIG. 16 shows a composite bone graft 700 in accordance with another embodiment. Composite bone graft 700 has many of the same features as bone graft 100. For brevity, identical or similar features will not be described. Bone graft 700 includes a first unit 720, a second unit 740 and a single connector 750 that interconnects the first and second units. Connector 750 has a cross section defining a pair of lobe-shaped ends 751 that are symmetrical to one another. As such, the cross section of connector 750 resembles the outline of the number 8. In addition, connector 750 extends in the longitudinal direction with respect to the bone graft, i.e. parallel to the long dimension. First unit 720 defines a recess 728 forming an undercut 729 designed to receive a first end 752 of connector 750. Second unit 740 similarly defines a recess 748 forming an undercut 749 designed to receive a second end 754 of connector 750 opposite the first end 752.

Figure 17:
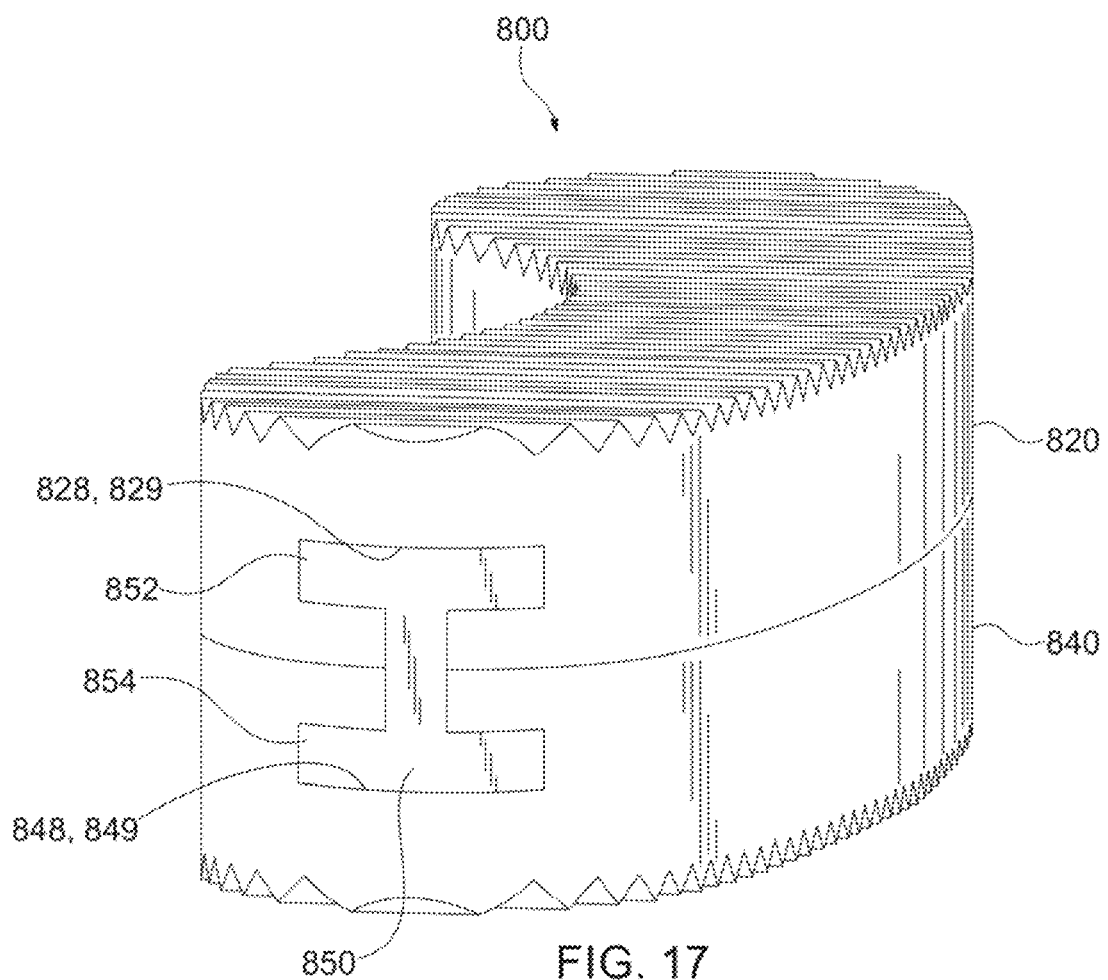
FIG. 17 is a perspective view of a bone graft in accordance with another embodiment of the invention.

FIG. 17 shows a composite bone graft 800 in accordance with another embodiment. Composite bone graft 800 has many of the same features as bone graft 100. For brevity, identical or similar features will not be described. Bone graft 800 includes a first unit 820, a second unit 840 and a single connector 850 that interconnects the first and second units. Connector 850 has an "I" shaped cross section. In addition, connector 850 extends in the longitudinal direction with respect to the bone graft, i.e. parallel to the long dimension. First unit 820 defines a recess 828 forming an undercut 829 designed to receive a first end 852 of connector 850. Second unit 840 similarly defines a recess 848 forming an undercut 849 designed to receive a second end 854 of connector 850 opposite the first end 852.

Figure 18:
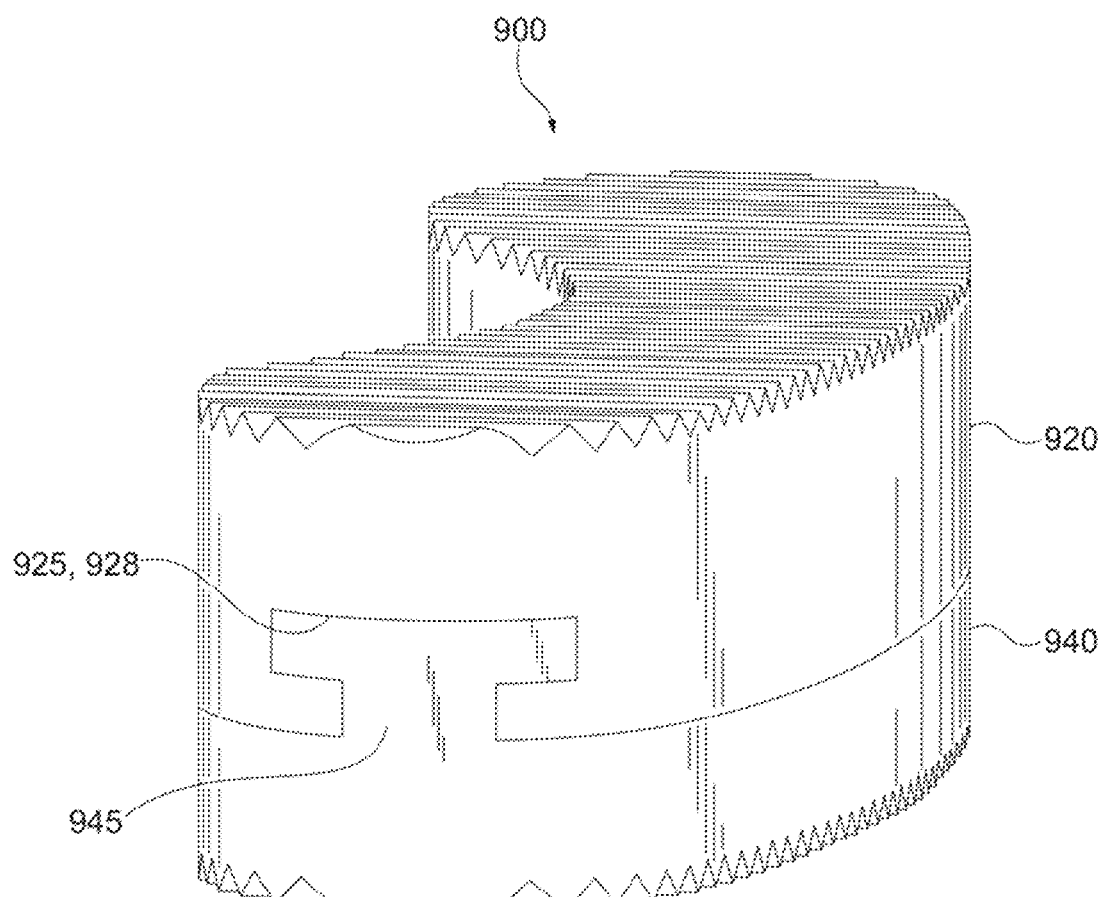
FIG. 18 is a perspective view of a bone graft in accordance with another embodiment of the invention.

FIG. 18 shows a composite bone graft 900 in accordance with another embodiment. Composite bone graft 900 has many of the same features as bone graft 100. For brevity, identical or similar features will not be described. Bone graft 900 includes a first unit 920 that interlocks directly with a second unit 940. As such, there is no separate connector in between first unit 920 and second unit 940. Second unit 940 has a "T"-shaped projection or key 945, while first unit 920 has an identically shaped "T"-shaped recess 925. Recess 925 forms an undercut 928 configured to receive projection 945 to interlock first unit and second unit together.

Many of the bone graft embodiments described thus far feature units that are interconnected in a vertically stacked arrangement. For example, bone graft 100 shown in FIGS. 1 and 2 has a first unit 120 vertically stacked above second unit 140. In this arrangement, the mating surface on each unit is located opposite the respective bone engagement surface of the unit. It will be understood that bone grafts in accordance with the invention need not have units stacked in a vertical arrangement, as other interlocking arrangements are contemplated in accordance with the invention.

Figure 19:
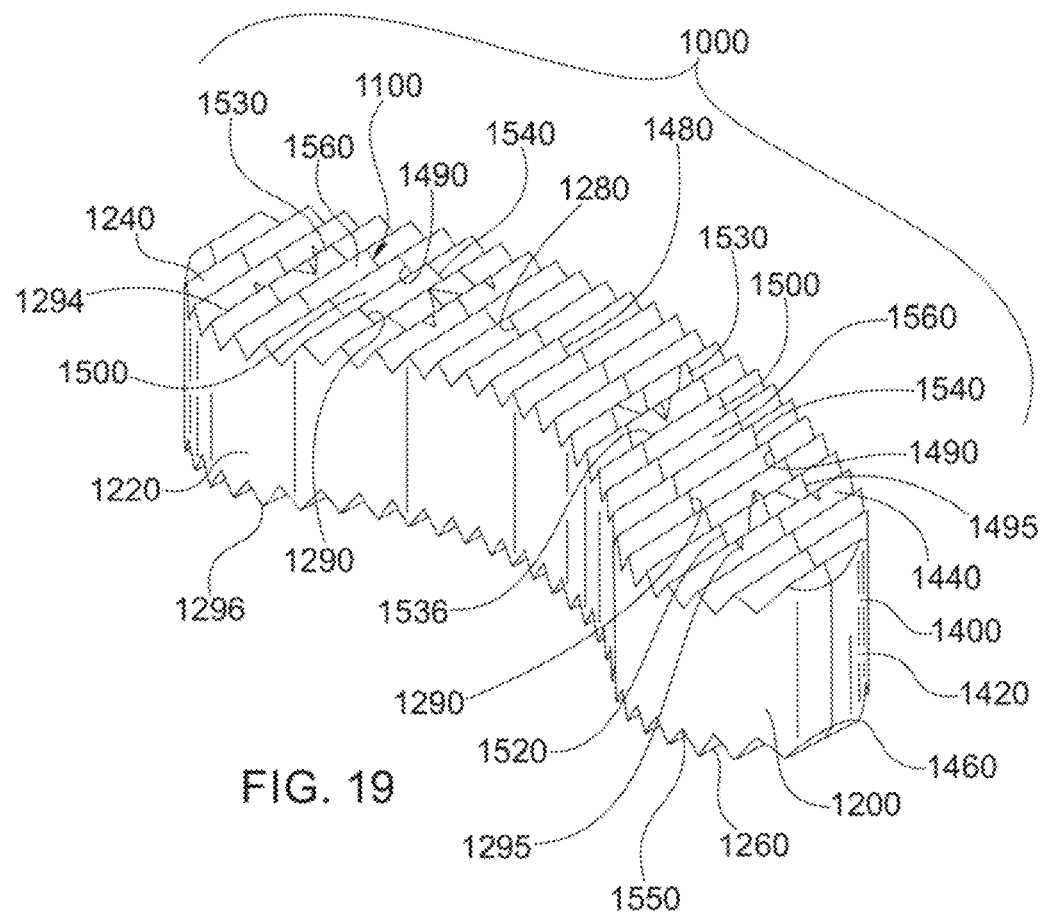
FIG. 19 is a perspective view of a bone graft in accordance with another embodiment of the invention.

For example, bone grafts in accordance with the invention can include first and second units that are joined laterally, or in a side-by-side arrangement, with respect to the spine. FIG. 19 shows one example of a bone graft 1000, which is identical in many respects to bone graft 100, but features parts that are joined laterally instead of vertically. Bone graft 1000 includes a first unit 1200 and a second unit 1400 interconnected with the first unit in a side-by-side arrangement. First unit 1200 is formed of a cortical bone portion 1220, and second unit 1400 is formed of a cortical bone portion 1420. First unit 1200 includes a superior or upper surface in the form of a bone engagement surface 1240 for contacting bone. Bone engagement surface 1240 has a series of parallel v-shaped ridges or projections 1294 for engaging bone. First unit 1200 also includes an inferior or lower surface in the form of a bone engagement surface 1260 opposite bone engagement surface 1240. Bone engagement surface 1260 has a series of parallel v-shaped ridges or projections 1296 for engaging bone.

Second unit 1400 is shown oriented in a mirror arrangement of first unit 1200. As such, second unit 1400 includes a superior or upper surface in the form of a bone engagement surface 1440 for contacting bone. Bone engagement surface 1440 has a series of parallel v-shaped ridges or projections 1494 for engaging bone. Second unit also includes an inferior or lower surface in the form of a bone engagement surface 1460 for contacting bone. Bone engagement surface 1460 has a series of parallel v-shaped ridges or projections 1496 for engaging bone. When first unit 1200 is interconnected with second unit 1400 as shown, bone engagement surfaces 1240 and 1440 form a continuous ridged surface to engage bone, and bone engagement surfaces 1260 and 1460 form a continuous ridged surface to engage bone.

First unit 1200 includes a mating surface 1280 lying in a curved plane that extends substantially orthogonal to the planes of bone engagement surface 1240 and bone engagement surface 1260. Similarly, second unit 1400 includes a mating surface 1480 lying in a curved plane that extends substantially orthogonal to the planes of bone engagement surface 1440 and bone engagement surface 1460. Mating surfaces 1280 and 1480 are configured to interconnect with one another, with mating surface 1280 in direct contact with mating surface 1480.

Interconnection of first unit 1200 and second unit 1400 is facilitated by a self-contained connection mechanism 1100 that resides completely within the first and second units. Connection mechanism 1100 includes at least one connection feature on each of the first unit and the second unit, and at least one connector that cooperatively engages or mates with each of the connection features on the first and second units. The at least one connector can take one of several forms, and the connection features on each of the first unit 1200 and second unit 1400 can also take one of several forms.

Connection mechanism 1100 includes two connection features on first unit 1200, two connection features on second unit 1400, and two discrete connectors or keys 1500 that engage with the connection features. Each connector 1500 can be formed of natural bone material, such as an allograft or autograft, and can be of the same or different material(s) used to form the first unit 1200 and the second unit 1400.

The two connection features on first unit 1200 are in the form of two recesses 1290 defined in mating surface 1280. Similarly, the two connection features on second unit 1400 are in the form of two recesses 1490 defined in mating surface 1480. Each connector 1500 has a first end 1520, a second end 1540 opposite the first end, and a middle portion 1560. In addition, each connector 1500 has an elongated body 1510 that terminates at a first end face 1530 at one end, and terminates at a second end face 1550 at the opposite end. First end face 1530 has a series of parallel v-shaped ridges or projections 1536 for engaging bone. Projections 1536 preferably have the same shape, size and arrangement as projections 1294 so that the projections conform to and blend with the projections, forming a continuous and uninterrupted series of ridges on the top of bone graft 1000. Likewise, second end face 1550 has a series of parallel v-shaped ridges or projections that are not visible in the Figure, but are identical in shape, orientation and arrangement as v-shaped ridges 1536. The projections on second end face 1550 preferably have the same shape, size and arrangement as projections 1296 so that the projections conform to and blend with the projections 1296, forming a continuous and uninterrupted series of ridges on the bottom of bone graft 1000. The cross section of each connector 1500 remains uniform along and throughout the entire length of the connector, remaining constant as it progresses from first end face 1530 to second end face 1550.

Each connector 1500 has a first end 1520 configured to engage one of the recesses 1290 in first unit 1200. Each connector 1500 also has a second end 1540 opposite first end 1520, the second end 1540 being configured to engage one of the recesses 1490 in second unit 1400. Each first end 1520 features one or more lateral projections, such that the width of the first end is greater than a maximum width of middle portion 1560. Likewise, each second end 1540 features one or more lateral projections, such that the width of the second end is greater than a maximum width of middle portion 1560.

Each of recesses 1290 is formed as an undercut 1295. Similarly, each of recesses 1490 is formed as an undercut 1495. Undercuts 1295 have cross sectional shapes that are substantially identical to the cross sectional shapes of first ends 1520, and undercuts 1495 have cross sectional shapes that are substantially identical to the cross sectional shapes of second ends 1540. In this arrangement, each undercut 1295 is adapted to receive a first end 1520 of one of the connectors 1500 in a longitudinal insertion direction parallel to the longitudinal axis of the undercut. Each undercut 1495 is likewise adapted to receive a second end 1540 of one of the connectors 1500 in a longitudinal insertion direction parallel to the longitudinal axis of the undercut.

Bone grafts in accordance with the invention can be implanted as stand-alone grafts, or in combination with other spinal implants. For example, bone grafts in accordance with the invention can be implanted in a vertebral space in conjunction with any of the spinal implants and fixation mechanisms disclosed in International Application No. PCT/US2014/030317, the contents of which is incorporated by reference herein in its entirety.

As described above, composite bone grafts in accordance with embodiments of the invention can include a substantially void central area, where the substantially void central area includes one or more therapeutically beneficial substances including but not limited to, for example, one or more of the following: osteoinductive substances, osteoconductive substances, and pharmaceutically active agents. Such therapeutically beneficial substances may optionally be provided with a carrier. Suitable osteoinductive substances include but are not limited to, for example, autograft bone; allograft bone; ViviGen® brand cellular bone matrix; ViviGen Formable™ brand cellular bone matrix, and the other substances previously listed. Such osteoinductive substances can be provided inside void spaces of the bone grafts, such as void 225 in bone graft 200 shown in FIG. 8. Alternatively, the osteoinductive substances can be provided adjacent one of the outer faces of the bone graft, such as adjacent the posterior face 543 of bone graft 500 shown in FIG. 14.

V. Surgical Implantation and Indications

The present composite bone graft is useful for implantation in patients suffering from defects caused by congenital anomaly, disease, or trauma, including for example, spine fractures; deformity, e.g. kyphotic deformities, e.g. posttraumatic kyphosis; postlaminectomy kyphosls, junctional kyphosis, and Scheuermann's kyphosis; scoliosis, e.g. neuromuscular scoliosis, adult scoliosis; paralytic scoliosis, congenital and syndromic scoliosis; and cervical neck pain. Surgical methods for correcting degenerative conditions, for example in the lumbar spine, include decompression (excision of disc material, hypertrophied bone, or ligament along with fusion, or fusion alone.

A lateral surgical approach is preferably used. The choice of approach is dictated by the site of primary pathology and the physical size of the composite bone graft. Pathology that involves vertebral bodies is best approached anteriorly through the thorax, abdomen or flank. Pathology involving posterior elements are best approached posteriorly for example, through a vertical midline approach or posterior lateral muscle spinning approach.

Those of ordinary skill in the art to which the present invention pertain, including for example an orthopaedic surgeon and a spinal surgeon, can readily select and employ a particular composite bone graft, without undue experimentation. Factors to be considered in such selection and employment include: the type and size of graft bone, its anatomic site of fusion, and the age of the patient. An ideal graft, for example for use in lumbar interbody fusion, should be: osteoinductive, non-immunogenic, provide immediate mechanical stability, and be appropriately sized and shaped for the particular application/patient. Indications, diagnostic criteria, graft selection and surgical technique, are factors that can be readily selected optimized and employed by those of ordinary skill in the art without undue experimentation, and are discussed in: Master Techniques in Orthopaedic Surgery, The Spine, edited by Bradford, David S., Lippincott-Raven, ISBN 0-7817-0033-7, Philadelphia, Pa., (1997), hereby incorporated herein by reference in its entirety. When implanting a cervical fusion graft, an anterior cervical approach is used.

While preferred embodiments of the invention have been shown and described herein, it will be understood that such embodiments are provided by way of example only. Numerous variations, changes and substitutions will occur to those skilled in the art without departing from the spirit of the invention. Moreover, embodiments of the invention encompass not only those examples illustrated in the drawing figures, but also other embodiments that combine features shown in the different examples. For example, embodiments of the invention include not only those bone grafts shown in FIGS. 1, 12 and 15, which lack a central void extending through the graft, but also include modified versions of the bone grafts shown in FIGS. 1, 12 and 15 that further include a central void such as void 250 shown in FIGS. 8 and 9. Accordingly, it is intended that the appended claims cover all such variations as fall within the spirit and scope of the invention.

What is claimed:

1. A spinal bone graft for implantation into a host, the spinal bone graft comprising:
one or more cortical bone portions forming a first unit, the first unit comprising a first bone engagement surface for contacting a first bone of the host, and a first mating surface opposite the first bone engagement surface, the first unit defining a first undercut extending from a first opening defined in the first mating surface;
one or more cortical bone portions forming a second unit, the second unit comprising a second bone engagement surface for contacting a second bone of the host, and a second mating surface opposite the second bone engagement surface, the second unit defining a second undercut extending from a second opening defined in the second mating surface, and
a connector having a first portion configured to be received within the first undercut and a second portion configured to be received within the second undercut such that the first unit and the second unit are coupled to each other via the connector and such that the first mating surface and the second mating surface face each other and are separated to define a void therebetween for receipt of a cellular bone matrix between the first mating surface and the second mating surface,
the first portion of the connector having a shape configured to be received within the first undercut such that, when disposed within the first undercut, the first portion is obstructed from passing through the first opening defined in the first mating surface by portions of the first unit defining the first undercut.

2. The spinal bone graft of claim 1, wherein the connector has a modified surface for promoting bone ingrowth.

3. The spinal bone graft of claim 1, wherein the first bone engagement surface and the second bone engagement surface include surface roughing or etching.

4. The spinal bone graft of claim 1, wherein the first bone engagement surface includes one or more surface projections.

5. The spinal bone graft of claim 4, wherein the one or more surface projections are arranged in a uniform pattern.

6. The spinal bone graft of claim 4, wherein the one or more surface projections are arranged in a non-uniform randomized pattern.

7. The spinal bone graft of claim 4, wherein the one or more surface projections include at least one of linear projections, pyramidal projections, spikes, round projections, trapezoidal projections or other protuberances.

8. The spinal bone graft of claim 7, wherein the one or more surface projections include linear projections, the linear projections being V-shaped.

9. The spinal bone graft of claim 1, wherein at least one of the first bone engagement surface or the second bone engagement surface includes a textured surface configured to promote bone ingrowth.

10. The spinal bone graft of claim 1, wherein the first undercut has a first cross-sectional shape and the first portion of the connector has a second cross-sectional shape configured to mate with the first cross-sectional shape such that the first undercut is configured to receive the first portion of the connector in an interlocking fit.

11. The spinal bone graft of claim 1, wherein the second portion of the connector has a shape configured to be received within the second undercut such that, when disposed within the second undercut, the second portion is obstructed from passing through the second opening defined in the second mating surface by portions of the second unit defining the second undercut.

12. The spinal bone graft of claim 1, wherein the connector is a first connector, further comprising a second connector having a first portion and a second portion, the first unit defining a third undercut configured to receive the first portion of the second connector, the second unit defining a fourth undercut configured to receive the second portion of the second connector.

13. The spinal bone graft of claim 1, further comprising the cellular bone matrix disposed in the void between the first mating surface and the second mating surface.

14. The spinal bone graft of claim 13, wherein the cellular bone matrix is disposed in contact with a portion of the connector disposed between the first mating surface and the second mating surface.

* * * * *